(12) United States Patent
Kline et al.

(10) Patent No.: US 8,382,736 B2
(45) Date of Patent: Feb. 26, 2013

(54) RELATIVE STIFFNESS FASTENERS

(75) Inventors: Mark James Kline, Okeana, OH (US); Anna Elizabeth Macura, Cincinnati, OH (US); Michael Gary Nease, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 570 days.

(21) Appl. No.: 11/638,988

(22) Filed: Dec. 14, 2006

(65) Prior Publication Data

US 2007/0143972 A1 Jun. 28, 2007

Related U.S. Application Data

(60) Provisional application No. 60/752,824, filed on Dec. 22, 2005.

(51) Int. Cl.
*A61F 13/15* (2006.01)
(52) U.S. Cl. .......... 604/387; 604/386; 604/385.03
(58) Field of Classification Search .......... 604/386–387, 604/389–390, 385.01, 385.03
See application file for complete search history.

(56) References Cited

U.S. PATENT DOCUMENTS

| | | |
|---|---|---|
| 3,860,003 A | 1/1975 | Buell |
| 3,911,173 A | 10/1975 | Sprague, Jr. |
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,673,402 A | 6/1987 | Weisman et al. |
| 4,695,278 A | 9/1987 | Lawson |
| 4,785,996 A | 11/1988 | Ziecker et al. |
| 4,834,735 A | 5/1989 | Alemany et al. |
| 4,842,666 A | 6/1989 | Werenicz |
| 4,846,815 A | 7/1989 | Scripps |
| 4,888,231 A | 12/1989 | Angstadt |
| 4,892,536 A | 1/1990 | DesMarais et al. |
| 4,909,803 A | 3/1990 | Aziz et al. |
| 4,940,464 A | 7/1990 | Van Gompel et al. |

(Continued)

FOREIGN PATENT DOCUMENTS

| | | |
|---|---|---|
| EP | 318087 B1 | 12/1991 |
| EP | 0734243 B1 | 6/2000 |

(Continued)

OTHER PUBLICATIONS

PCT International Search Report.

*Primary Examiner* — Michele M Kidwell
(74) *Attorney, Agent, or Firm* — Laura L. Whitmer; Christian M. Best

(57) ABSTRACT

A fastening member has an inboard end and an outboard end and a panel region, an end region, and a fastening element. The panel region has a proximal edge and a distal edge. The panel region is disposed adjacent to the inboard end and is more extensible than the end region. The end region is disposed adjacent to the outboard end. The end region has a fastening element zone having a first stiffness and an intermediate zone having a second stiffness. The first stiffness is greater than the second stiffness. The intermediate zone is disposed between the fastening element zone and the panel region adjacent to the distal edge. The fastening element is disposed in the end region and defines the fastening element zone.

16 Claims, 23 Drawing Sheets

U.S. PATENT DOCUMENTS

| | | | |
|---|---|---|---|
| 4,968,312 A | 11/1990 | Khan | |
| 4,990,147 A | 2/1991 | Freeland | |
| 5,006,394 A | 4/1991 | Baird | |
| 5,019,073 A | 5/1991 | Roessler et al. | |
| 5,037,416 A | 8/1991 | Allen et al. | |
| 5,062,840 A | 11/1991 | Holt et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,176,671 A | 1/1993 | Roessler et al. | |
| 5,221,274 A | 6/1993 | Buell et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,306,266 A | 4/1994 | Freeland | |
| 5,312,387 A | 5/1994 | Rossini et al. | |
| 5,318,555 A | 6/1994 | Siebers et al. | |
| 5,342,338 A | 8/1994 | Roe | |
| 5,380,313 A | 1/1995 | Goulait et al. | |
| 5,387,207 A | 2/1995 | Dyer et al. | |
| 5,397,318 A | 3/1995 | Dreier | |
| 5,399,219 A | 3/1995 | Roessler et al. | |
| 5,407,439 A | 4/1995 | Goulait | |
| 5,460,622 A | 10/1995 | Dragoo et al. | |
| 5,496,298 A | 3/1996 | Kuepper et al. | |
| 5,514,121 A | 5/1996 | Roe et al. | |
| 5,518,801 A | 5/1996 | Chappell et al. | |
| 5,540,671 A | 7/1996 | Dreier | |
| 5,540,673 A | 7/1996 | Thomas et al. | |
| 5,542,942 A | 8/1996 | Kline et al. | |
| 5,549,591 A * | 8/1996 | Landvogt | 604/389 |
| 5,549,592 A | 8/1996 | Fries et al. | |
| 5,554,142 A | 9/1996 | Dreier et al. | |
| 5,569,233 A | 10/1996 | Goulait | |
| 5,569,234 A | 10/1996 | Buell et al. | |
| 5,571,096 A | 11/1996 | Dobrin et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,653,703 A | 8/1997 | Roe et al. | |
| 5,669,900 A | 9/1997 | Bullwinkel et al. | |
| 5,685,873 A | 11/1997 | Bruemmer | |
| H1732 H | 6/1998 | Johnson | |
| 5,759,317 A | 6/1998 | Justmann | |
| 5,865,823 A | 2/1999 | Curro | |
| 5,897,545 A | 4/1999 | Kline et al. | |
| 5,900,101 A | 5/1999 | Justmann | |
| 5,904,675 A | 5/1999 | Laux et al. | |
| 5,938,648 A | 8/1999 | LaVon et al. | |
| 5,941,864 A | 8/1999 | Roe | |
| 5,957,908 A | 9/1999 | Kline et al. | |
| 5,968,025 A | 10/1999 | Roe et al. | |
| 5,977,430 A | 11/1999 | Roe et al. | |
| 5,993,433 A | 11/1999 | St. Louis et al. | |
| 5,997,520 A | 12/1999 | Ahr et al. | |
| 6,010,490 A | 1/2000 | Freeland et al. | |
| 6,013,063 A | 1/2000 | Roe et al. | |
| 6,120,487 A | 9/2000 | Ashton | |
| 6,120,489 A | 9/2000 | Johnson et al. | |
| 6,156,424 A | 12/2000 | Taylor | |
| 6,168,584 B1 | 1/2001 | Allen et al. | |
| 6,225,236 B1 | 5/2001 | Nishimoto et al. | |
| 6,235,137 B1 | 5/2001 | Van Eperen et al. | |
| 6,248,097 B1 | 6/2001 | Beitz et al. | |
| 6,454,753 B1 | 9/2002 | Shimoe et al. | |
| 6,623,469 B1 | 9/2003 | Thomas | |
| 6,652,693 B2 | 11/2003 | Burriss et al. | |
| 6,680,422 B2 | 1/2004 | Roe | |
| 6,716,441 B1 | 4/2004 | Osborne et al. | |
| 7,195,729 B2 | 3/2007 | Jackson et al. | |
| 2001/0053905 A1 | 12/2001 | Shingu et al. | |
| 2003/0077430 A1 | 4/2003 | Grimm et al. | |
| 2003/0088220 A1 | 5/2003 | Molander et al. | |
| 2003/0100879 A1 | 5/2003 | Kline et al. | |
| 2003/0109844 A1 * | 6/2003 | Gibbs | 604/389 |
| 2003/0233082 A1 | 12/2003 | Kline et al. | |
| 2004/0063369 A1 | 4/2004 | Ahn et al. | |
| 2004/0116888 A1 | 6/2004 | Dorschner | |
| 2004/0122413 A1 | 6/2004 | Roessler et al. | |
| 2004/0181200 A1 | 9/2004 | Desai et al. | |
| 2004/0193133 A1 | 9/2004 | Desai et al. | |
| 2005/0004547 A1 | 1/2005 | Lavash | |
| 2005/0009173 A1 | 1/2005 | Amand | |
| 2005/0027267 A1 | 2/2005 | Van Dyke et al. | |
| 2005/0249915 A1 | 11/2005 | Wood et al. | |
| 2006/0292328 A1 | 12/2006 | Baldauf et al. | |
| 2007/0157441 A1 | 7/2007 | Kline et al. | |

FOREIGN PATENT DOCUMENTS

| | | |
|---|---|---|
| JP | 10-155834 | 12/1996 |
| JP | 2001/145663 A | 5/2001 |
| WO | WO94/14395 A1 | 7/1994 |
| WO | WO-95/16746 A1 | 6/1995 |
| WO | WO95/24173 A2 | 9/1995 |
| WO | WO-03/082167 A2 | 10/2003 |
| WO | WO2004/030763 A2 | 4/2004 |
| WO | WO2004/082918 A2 | 9/2004 |
| WO | WO-2005/110731 A2 | 11/2005 |

* cited by examiner

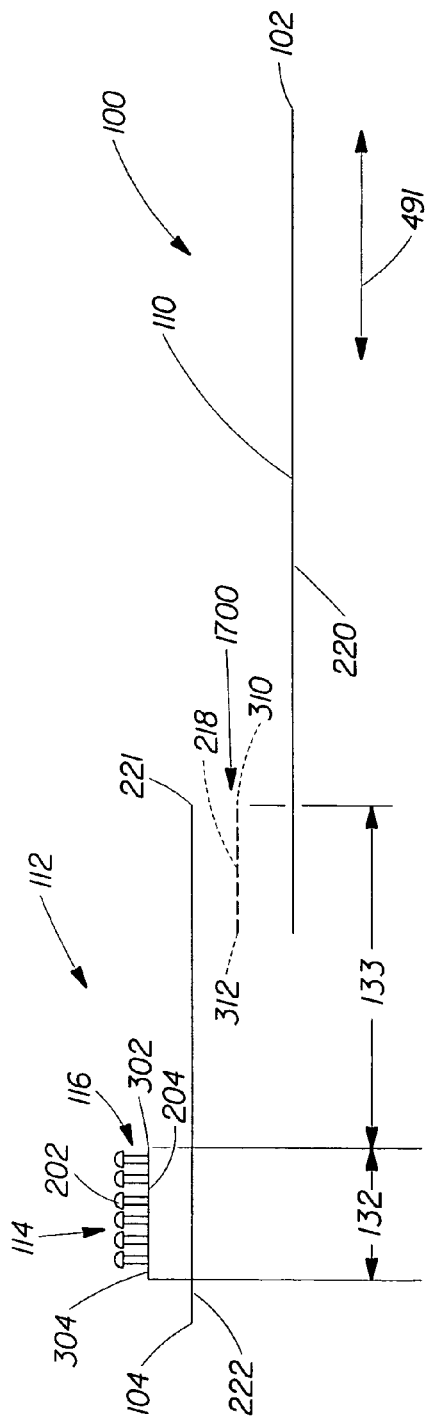
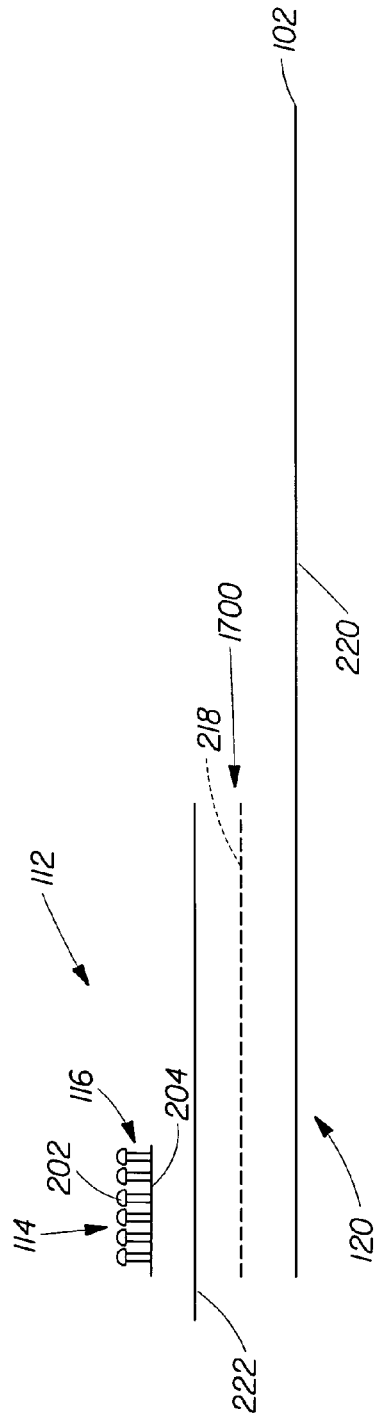
Fig. 3A
Fig. 3B

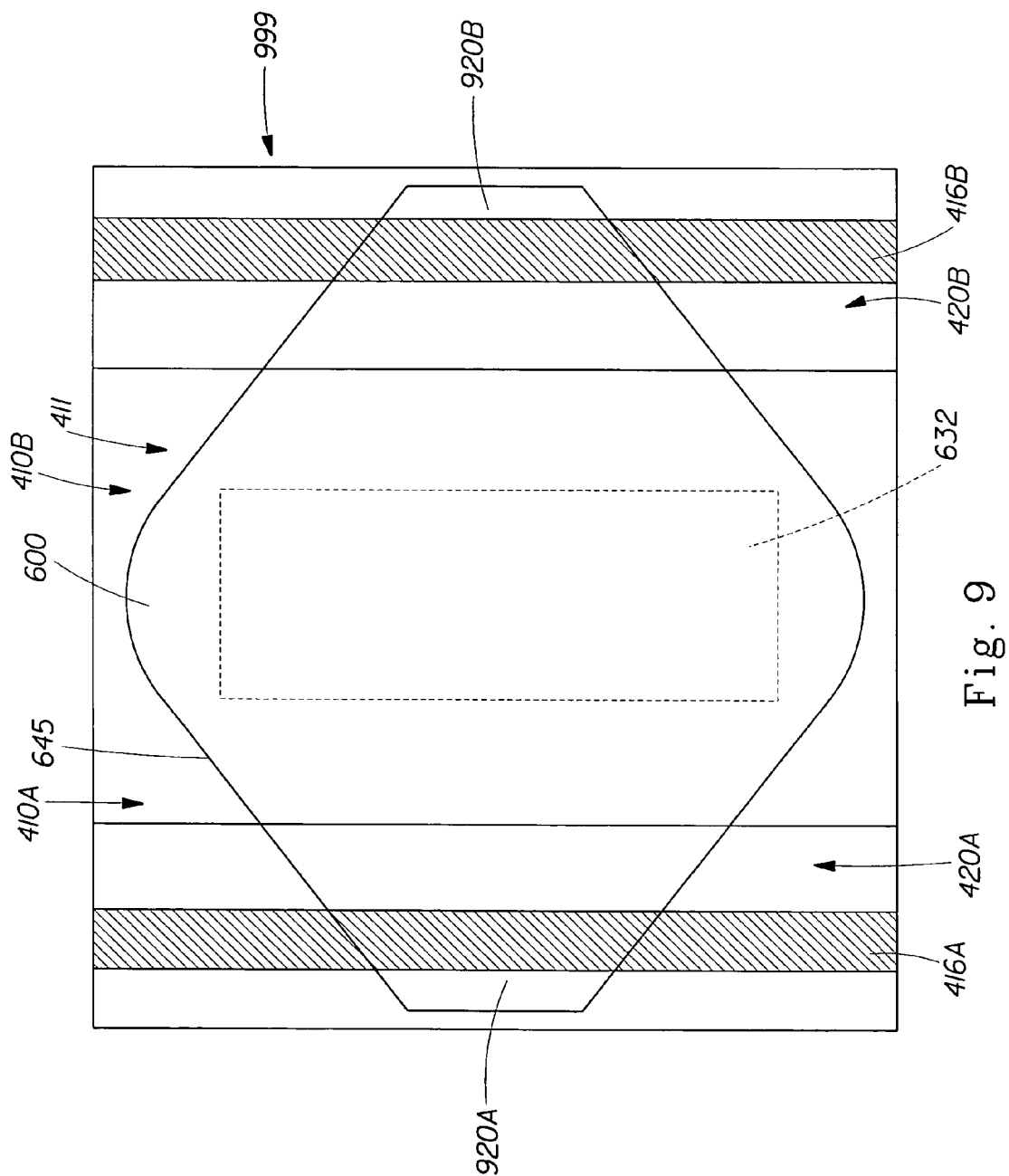

RELATIVE STIFFNESS FASTENERS

CROSS REFERENCE TO RELATED APPLICATIONS

This application claims the benefit of U.S. Provisional Application No. 60/752,824, filed on Dec. 22, 2005.

FIELD OF THE INVENTION

The present invention relates to fastening members. Particularly, the present invention relates to fastening members having surface fastening elements and to fastening members having a portion which has increased resistance to buckling under applied load.

BACKGROUND OF THE INVENTION

Refastenable mechanical fastening systems can be used in a wide number of applications. For example, such refastenable fastening systems can be used to connect one portion of a disposable absorbent article to another portion of the disposable absorbent article.

In general, mechanical fastening systems may comprise a fastening member having a receiving/female component and/ or a fastening member having an engaging/male component. In some mechanical fastening systems, the engaging component comprises a plurality of hook elements, and the receiving component comprises a plurality of loop elements. In a fastened state, the hook elements typically are entangled with the loop elements such that a connection between the engaging and receiving components is formed.

During fastening, a tension can be applied to the fastening member. The applied tension can induce compressive forces in the fastening member which can cause a portion of the fastening member to contract (neck). Additionally, the compressive forces can often act on the engaging component and cause the engaging component to buckle.

Unfortunately, when buckled, the hook elements of the engaging component can be out of alignment, e.g. not in the same plane. This misalignment of hook elements can cause less than 100% of the hook elements to engage with the receiving component thereby reducing the performance of the fastening system.

Consequently, a need exists for a fastening member which can provide increased resistance to buckling forces.

SUMMARY OF THE INVENTION

A fastening member constructed in accordance with the present invention may provide improved fastening capability. The fastening member constructed in accordance with the present invention has an inboard end and an outboard end and comprises a panel region, an end region, and a fastening element. The panel region is disposed adjacent to the inboard end and is more extensible than the end region.

The end region is disposed adjacent to the outboard end. The end region comprises a fastening element zone having a first stiffness and an intermediate zone having a second stiffness. The intermediate zone is disposed between the fastening element zone and the panel region adjacent to an interface between the panel region and the end region. The fastening element is disposed in the end region and defines the fastening element zone.

The present invention further pertains to a web of fastening members. In some embodiments, the web of fastening members has a first longitudinal edge and a second longitudinal edge. The web of fastening members further comprises a first panel, a second panel, and an end area. The first panel region is disposed adjacent to the first longitudinal edge. The second panel region is disposed adjacent to the second longitudinal edge. The end area is disposed between the first panel region and the second panel region.

The end area comprises a fastening element, a first intermediate zone, and a second intermediate zone. The fastening element defines a fastening element zone having a first stiffness. The first intermediate zone is disposed between the fastening element zone and the first panel region and has a second stiffness. The second intermediate zone is disposed between the fastening element zone and the second panel region and has a third stiffness.

The first panel region and the second panel region are more extensible than the end area. The first stiffness is greater than the second stiffness and greater than the third stiffness.

A method of shaping a fastening member comprises the steps of providing a siamese web of fastening members to a separation device. The siamese web of fastening members is separated along a siamese separation line, thereby creating a plurality of single repeating unit webs and thereby creating a first trim piece. A fastening member is separated from a single repeating unit web along a leading edge thereby creating a second trim piece. The fastening member is also separated from the single repeating unit web along a trailing edge thereby creating a third trim piece. The first trim piece, the second trim piece, and the third trim piece are removed.

BRIEF DESCRIPTION OF THE DRAWINGS

FIG. 3A is a cross sectional view showing the association of an end region with a panel region of the fastening member of FIG. 1A as seen through line 3A-3A.

FIGS. 3B-3D are cross sectional views showing other embodiments of the association of an end region with a panel region of the fastening member of FIG. 1A.

FIG. 9 is a plan view showing a sanitary napkin constructed in accordance with the present invention on a parent web.

DETAILED DESCRIPTION OF THE INVENTION

Figure 1A:
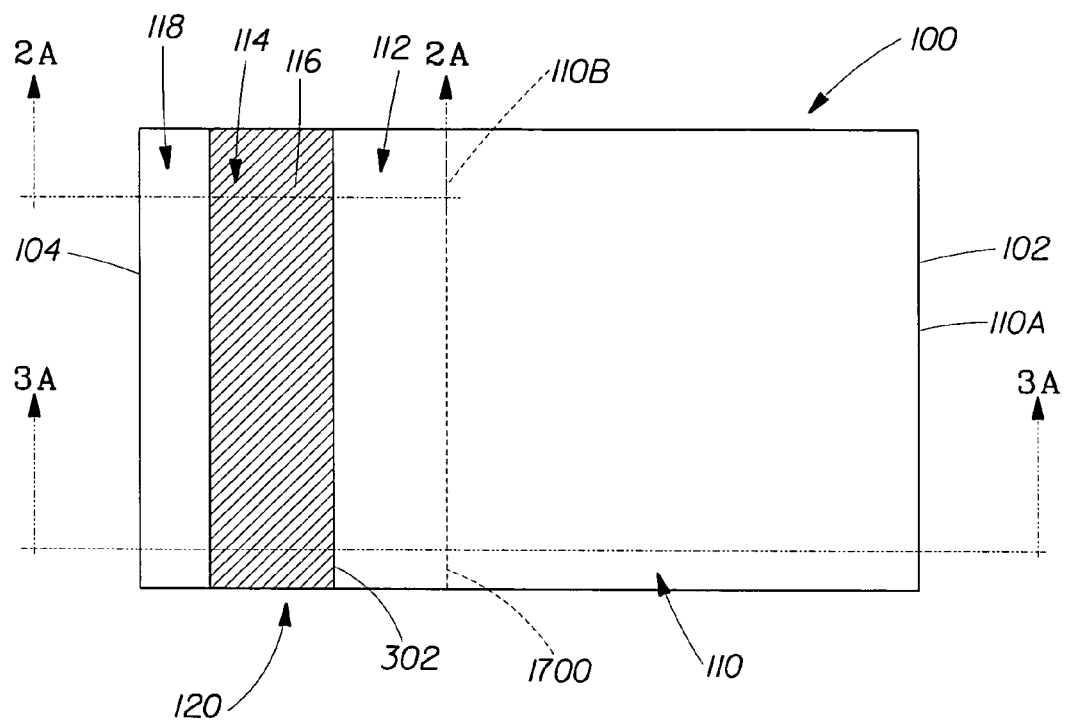
FIG. 1A is a plan view showing a fastening member constructed in accordance with the present invention.

Definitions:

As used herein, the terms "absorbent article" and "article" refer to a wearable device that absorbs and/or contains liquid and, more specifically, refers to a device that is placed against or in proximity to the body of the wearer to absorb and contain the various exudates discharged from the body. Suitable examples include diapers, training pants, refastenable pants, pull-on garments, adult incontinence products and feminine care products such as sanitary napkins. Furthermore, the terms "absorbent article" and "article" include a "disposable absorbent article" which is intended to be discarded and not laundered or otherwise restored after no more than ten uses, preferably after no more than five uses, and most preferably after a single use (although certain components may be recycled, reused, or composted).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein "elastically extensible" refers to characteristics of extensible materials that have the ability to return to approximately their original dimensions after a force that extended the extensible material is removed.

The terms "exterior surface" and "interior surface" as used herein refer to relative locations on a portion of a fastening member as shown. The terms "exterior surface" and "interior surface" are not necessarily indicative of locations with respect to the fastening member after the fastening member has been joined to an article.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element.

The term "longitudinal" is used herein to refer to a direction which is generally parallel to the longest edge of an element except where otherwise noted. In the context of disposable absorbent articles, a "longitudinal" direction "runs substantially perpendicular from a waist edge to an opposing waist edge of the article and generally parallel to the maximum linear dimension of the article. Directions within ±45 degrees of the longitudinal direction are considered to be "longitudinal".

The term "lateral" refers to a direction running generally perpendicular to and in the same plane as the "longitudinal" direction. In the context of disposable absorbent articles, a "lateral" direction runs from one longitudinal edge of the article to an opposing longitudinal edge of the article. Directions within ±45° of the lateral direction are considered to be "lateral".

The terms "machine direction" or "MD" refer to a direction which is generally parallel to the forward direction of a material, member, element, item, etc. through a process. For example, nonwovens are typically formed with a machine direction that corresponds to the long or rolled direction of fabrication. The machine direction can also be the primary direction of fiber orientation in the nonwoven.

The terms "cross direction" or "CD" refer to a direction which is generally perpendicular to and in the same plane as the machine direction.

The terms "pant", "training pant", "closed diaper", "prefastened diaper", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

Description:

Fastening Members

The fastening member of the present invention may provide improved fastening capability. The fastening member of the present invention may be incorporated into a variety of consumer and commercial goods that may benefit from having a fastening member constructed in accordance with the present invention. In any of the embodiments described herein, the fastening member may be a separate element added to the commercial good. For example, the fastening member may be a discrete structure joined to any component (e.g., a topsheet, an absorbent core, a backsheet, a fastening system, a cuff, etc.) of an absorbent article or other commercial good (e.g., a wrap, a medical product, etc.). Alternatively, the fastening member may be constructed as part or all of any element of the commercial good or fastener. For example, the fastening member may be constructed as part or all of any component (e.g., a topsheet, an absorbent core, a backsheet, a fastening system, a cuff, etc.) of an absorbent article or other commercial good (e.g., a wrap, a medical product, etc.). Further, the fastening member may be disposed in any suitable location on or in the commercial good or fastener. For example, the fastening member may be disposed on a garment-facing surface of, body-facing surface of, or contained within the commercial good or fastener.

As shown in FIG. 1A, a fastening member 100 constructed in accordance with the present invention may comprise an inboard end 102 and an outboard end 104. The fastening member 100 may further comprise a panel region 110 and an end region 120. The panel region 110 and the end region 120 are separated by an interface 1700 which comprises a distal end 110B of the panel region 110. The panel region 110 can be disposed adjacent to the inboard end 102 of the fastening member 100. The panel region 110 may further comprise a proximal edge 110A and the distal edge 110B. As shown, the proximal edge 110A can be disposed adjacent to the inboard end 102.

In some embodiments, the panel region 110 can be elastically extensible. In some embodiments, the panel region 110 may be extensible but not elastically extensible. For example, the panel region 110 may lack the ability to return to approximately its original dimensions after a force that extended the panel region is removed.

The panel region 110 can be more extensible than the end region 120. For example, in some embodiments, the panel region 110 can extend to greater than or equal to about 100% at an applied load of about 0.5 N/cm. In some embodiments, the panel region 110 can extend to greater than or equal to about 100% at an applied load of about 1.5 N/cm. In some embodiments, the panel region 110 can extend to greater than or equal to about 100% at an applied load of about 4.0 N/cm. In some embodiments, the panel region 110 can extend to greater than or equal to about 150% at an applied load of about 0.5 N/cm. In some embodiments, the panel region 110 can extend to greater than or equal to about 150% at an applied load of about 1.5 N/cm. In some embodiments, the panel region 110 can extend to greater than or equal to about 150% at an applied load of about 4.0 N/cm.

In contrast, the end region 120 can extend to less than about 100% at an applied load of about 4.0 N/cm, in some embodiments. In some embodiments, the end region 120 can extend to less than about 50% at the applied load mentioned above. In some embodiments, the end region 120 can extend to less than about 15% at the applied load mentioned above.

The end region 120 can be disposed adjacent to the outboard end 104 of the fastening member 100 and adjacent to the distal edge 110B of the panel region 110. The end region 120 may comprise a fastening element zone 114 and an intermediate zone 112. The intermediate zone 112 can be disposed between the fastening element zone 114 and the panel region 110. As shown, in some embodiments, the intermediate zone 112 can be disposed adjacent to the interface 1700 of the panel region 110.

In some embodiments, the end region 120 may further comprise a grip zone 118 which is disposed between the fastening element zone 114 and the outboard end 104. The grip zone 118 can aid a user in handling the fastening member 100. For example, where the fastening member 100 is attached to a disposable diaper, the grip zone 118 can aid the user in grasping the fastening member 100 such that the overall process of fastening is facilitated. The grip zone 118 can be an extension of the end region 120 or can be a discrete component attached to the end region 120.

The fastening element zone 114 can be defined by a perimeter of a fastening element 116 which is disposed in the end region 120. The fastening element zone 114 includes all layers which are subjacent and/or superjacent to the fastening element 116. The fastening element 116 can be joined to the end region 120 by any suitable means. Exemplary means for joining the fastening element 116 to the end region are discussed hereafter with regard to FIGS. 2A-2J.

The fastening element zone 114 can have a first stiffness which can be greater than about 1000 N/m, in some embodiments. In some embodiments the first stiffness can be greater than about 1500 N/m. In some embodiments, the first stiffness can be greater than about 2500 N/m. In some embodiments, the first stiffness can be in a range from between about 1000 N/m to about 7000 N/m or any individual number within the range. In some embodiments, the first stiffness can be in a range from about 1500 N/m to about 6000 N/m. In other embodiments, the first stiffness can be in a range from about 2500 N/m to about 5000 N/m.

The stiffness of the fastening element zone 114 can provide a more stable fastening member 100 in the fastening element zone 114. For example, under an applied fastening load, typically a tension load, conventional fastening members and fastening elements can buckle. However, because the fastening element zone 114 can have a greater stiffness than a corresponding fastening element zone in a conventional fastening member, the fastening element zone 114 can be more resistant to buckling when the fastening force is applied to the fastening member 100. Because the fastening element zone 114 may be more resistant to buckling, it is believed that more of the fastening element 116 can engage its target surface thereby providing improved fastening performance.

A portion of the intermediate zone 112 can have a second stiffness which can be less than the first stiffness. For example, in some embodiments, the second stiffness can be less than about 1000 N/m. In some embodiments, the second stiffness can be greater than about 200 N/m. In some embodiments, the second stiffness can be greater than about 300 N/m. In some embodiments, the second stiffness can be greater than about 400 N/m. In some embodiments, the second stiffness can be in a range from about 200 N/m to about 1000 N/m or any individual number within the range. In some embodiments, the second stiffness can be in a range from about 300 N/m to about 750 N/m. In some embodiments, the second stiffness can be in a range from about 400 N/m to about 600 N/m.

The portion of the intermediate zone 112 having the second stiffness can be disposed adjacent to the interface 1700 between the panel region 110 and the end region 120. Additionally, in some embodiments, the portion of the intermediate zone 112 having the second stiffness can be disposed inward toward the inboard end 102 from an inner edge 302 of the fastening element 116. For example, in some embodiments, the portion can be disposed inward at least about 10% of an intermediate zone width 133 (shown in FIG. 1B) from the inner edge 302 of the fastening element 116. In some embodiments, the portion can be disposed inward at least about 25% of the intermediate zone width 133 (shown in FIG. 1B) from the inner edge 302 of the fastening element 116. In some embodiments, the portion can be disposed inward at least about 50% of the intermediate zone width 133 (shown in FIG. 1B) from the inner edge 302 of the fastening element 116. In some embodiments, the portion can be disposed inward at least about 75% of the intermediate zone width 133 (shown in FIG. 1B) from the inner edge 302 of the fastening element 116. In some embodiments, the portion can be disposed inward at least about 95% of the intermediate zone width 133 (shown in FIG. 1B) from the inner edge 302 of the fastening element 116.

The intermediate zone 112 is not limited to having only a portion with the second stiffness. In some embodiments, the entire intermediate zone 112 may comprise the second stiffness. However, in other embodiments, the intermediate zone 112 may comprise a stiffness gradient. For example, a first portion of the intermediate zone 112 proximate to the fastening element zone 114 may comprise a stiffness which is equal to the first stiffness, e.g. greater than about 1000 N/m. In contrast, a second portion of the intermediate zone 112 proximate to the interface 1700 between the panel region 110 and the end region 120 may comprise a stiffness which is equal to the second stiffness, e.g. less than about 1000 N/m. A third portion of the intermediate zone 112, disposed between the first portion and the second portion can have a stiffness which is between the first stiffness and the second stiffness. As another example, the stiffness of the intermediate zone 112 may vary continuously from the inner edge 302 to the second portion of the intermediate zone 112 proximate to the interface 1700. In these embodiments, the stiffness may increase and/or decrease.

The reduced stiffness in the portion of the intermediate zone 112 can provide improved comfort for the wearer. For example, in some embodiments, the fastening member 100 can be attached to a disposable absorbent article such that the intermediate zone 112 is positioned in a high movement area of a wearer. In these instances, an increased stiffness, e.g. greater than about 1000 N/m, can cause redmarking on the wearer because the intermediate zone of the fastening member would be more resistant to buckling. In contrast, a portion of the intermediate zone 112 of the present invention has decreased stiffness, e.g. less than about 1000 N/m, thereby allowing the portion of the intermediate zone 112 to more readily buckle instead of poking the skin of the wearer.

Additionally, in some embodiments, the panel region 110 may have a third stiffness. The third stiffness can be less than about 250 N/m, in some embodiments. In other embodiments, the third stiffness can be less than about 150 N/m. In other embodiments, the third stiffness can be less than about 100 N/m. In some embodiments, the third stiffness can be less than the second stiffness. In some embodiments, the third stiffness can be equal to the second stiffness.

One advantage of having a reduced stiffness in the panel region 110 as compared to the fastening element zone 114 is that the reduced stiffness panel region can be cheaper to manufacture. Typically, increased costs can be incurred as a result of increasing the amount of stiffness in a fastening member. By limiting the added stiffness to specific portions of the fastening member of the present invention, increased performance and reduced costs may be achieved.

As mentioned above, the fastening members of the present invention can be joined to a disposable absorbent article such that the fastening member is subjected to much movement of the wearer, in some embodiments. For example, fastening members of the present invention can be joined to a disposable diaper as a side panel, in some embodiments. Because the side panels are typically located in high movement areas of the disposable diaper, another advantage of having a reduced stiffness in the panel region 110, compared to the fastening element zone 114, is that the reduced stiffness panel region may conform to the wearer much easier than a stiffer material would. Additionally, because the fastening member is in a high movement area of the disposable diaper, a stiffer panel region could potentially cause red marking on the skin of the wearer.

Figure 1B:
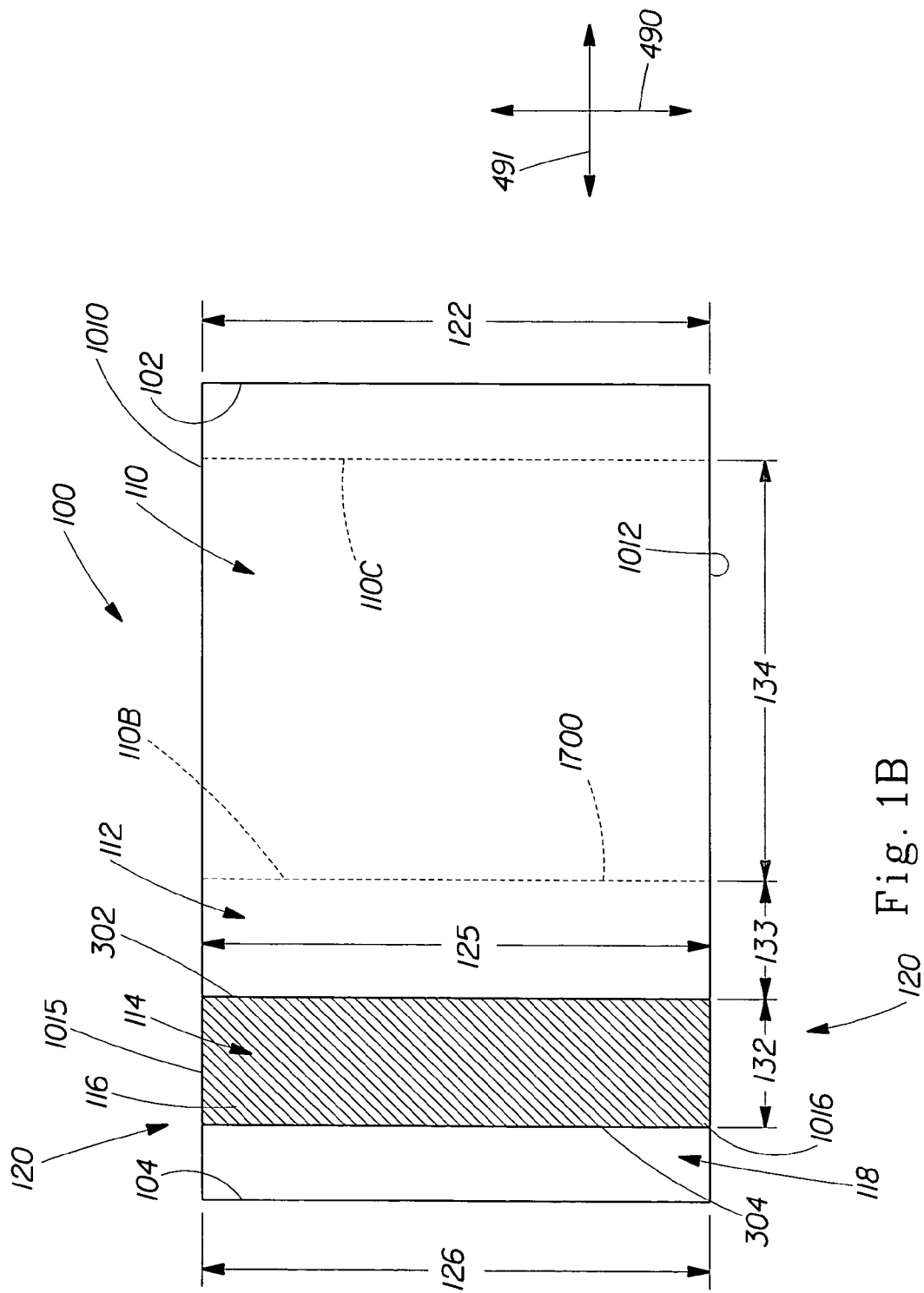
FIG. 1B is a plan view showing additional features of the fastening member of FIG. 1A.

As shown in FIG. 1B, the fastening member 100, adjacent the inboard end 102, can have a fastening member length 122. The end region 120 adjacent to the interface 1700 can have an end region length 125, and the fastening element 116 can have a fastening element length 126. The fastening member length 122 is the maximum linear distance between a leading edge 1010 and a trailing edge 1012. The end region length 125 is the maximum linear distance between the leading edge 1010 and the trailing edge 1012 adjacent to the interface 1700. The fastening element length 126 is the maximum linear distance between a first end edge 1015 and a second end edge 1016 of the fastening element 116. The maximum linear distances mentioned above are generally parallel to a first direction 490.

In some embodiments, the fastening member length 122 can be equal to the end region length 125, and the fastening element length 126 can be equal to the end region length 125. In some embodiments, the fastening element length 126 can be less than the end region length 125 which is less than the fastening member length 122. For example, the fastening element length 126 can be less than or equal to about 90% of the end region length 125. As another example, the fastening element length 126 can be less than or equal to about 80% of the end region length 125. As yet another example, the fastening element length 126 can be less than or equal to about 50% of the end region length 125. As yet another example, the fastening element length 126 can be less than or equal to about 90% of the fastening member length 122. As yet another example, the fastening element length 126 can be less than or equal to about 80% of the fastening member length 122. As yet another example, the fastening element length 126 can be less than or equal to about 50% of the fastening member length 122.

As shown, the intermediate zone 112 may have an intermediate zone width 133 and the fastening element 116 can have a fastening element width 132. The intermediate zone width 133 is the maximum linear distance between the interface 1700 and the inner edge 302 of the fastening element 116. The fastening element width 132 is the maximum linear distance between the inner edge 302 and an outer edge 304 of the fastening element 116. The maximum linear distances for the intermediate zone width 133 and the fastening element width 132, are generally parallel to a second direction 491. In some embodiments, the interface 1700 between the panel region 110 and the end region 120 can be defined by the inwardmost point 221 (shown in FIG. 3A) of the first substrate 222.

In some embodiments, the first direction 490 can be generally parallel to a machine direction. In some embodiments, the second direction 491 can be generally parallel to a cross machine direction. In some embodiments, the first direction 490 can be generally parallel to the second direction 491.

Depending on the specific embodiment, the interface 1700 between the panel region 110 and the end region 120 can be determined in various ways. In general, the interface 1700 can be located at a point where the extensibility of the panel region 110 is eliminated or substantially reduced as compared to the extensibility of the remainder of the panel region 110. In some embodiments, "substantially reduced" means the percentage extension is at least 25% lower than the highest extensibility measured in the panel region 110. In some embodiments, "substantially reduced" means the percentage extension is at least 50% lower than the highest extensibility measured in the panel region 110. In some embodiments, one skilled in the art can readily identify such a transition by merely pulling on a fastening member and observing where extension occurs and where little or no extension occurs. Further, by observing the extensibility method applied to the entire fastening member, one can more directly identify the interface 1700.

In some instances, the interface 1700 can be associated with physical attributes of the fastening member. For example, in some embodiments using zero-strain laminates to achieve the panel region's extensibility, the interface 1700 is the first visible line of activation adjacent the fastening element zone 114. In some embodiments using live stretch (e.g., an elastomer that has been pre-tensioned before being joined to one or more other substrate and results in a corrugation of the one or more other substrates once the tension applied to the elastomer is relieved), the interface 1700 can be at the first visible corrugation adjacent to the fastening element zone 114. In some embodiments, where the end region 120 comprises a stiffening element, e.g. a first substrate 222 (shown in FIGS. 2C, 2D, and 2J), a base substrate 220 (shown in FIGS. 2A-2J), a first bonding agent 218 (shown in FIGS. 2A-2E and 2J), etc., which is disposed in the end region 120 and extend inward from the inner edge 302 of the fastening element 116, the interface 1700 may be at the innermost edge of the stiffening element. In some embodiments using a stiffener that extends to the panel region 110 (such as the first substrate 222, the base substrate 230, and/or the bonding agent 218, etc) yet have a varying basis weight and/or thickness, the interface 1700 may be at a transition in basis weight and/or thickness.

In some embodiments, the intermediate zone width 133 can be greater than about zero percent of the fastening element width 132. In some embodiments, the intermediate zone width 133 can be greater than about 25% of the fastening element width 132. In some embodiments, the intermediate zone width 133 can be greater than about 50% of the fastening element width 132. In some embodiments, the intermediate zone width 133 can be greater than about 100% of the fastening element width 132. The fastening element width 132 and the intermediate zone width 133 are discussed further with regard to FIG. 3A.

As stated previously, the fastening element 116 defines the fastening element zone 114. Consequently, the fastening element width 132 is also the width of the fastening element zone 114. Similarly, the fastening element length 126 is also the length of the fastening element zone 114.

As stated previously, the fastening element zone 114 can have an increased stiffness compared to the intermediate zone 112 and, in some embodiments, when compared to the stiffness of the panel region 110. The stiffness of the fastening element zone 114 can be increased by any suitable means. Examples of suitable means of increasing the stiffness of the fastening element zone 114 are discussed with regard to FIGS. 2A-2J.

Figure 2A:
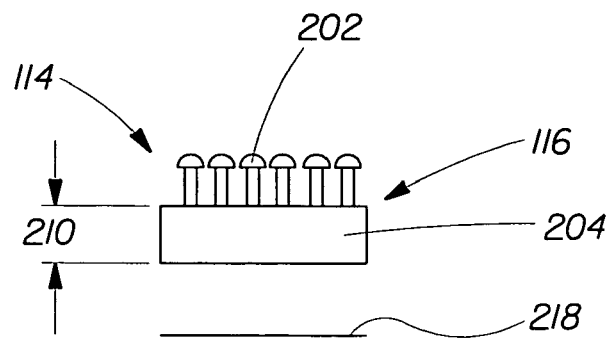
FIG. 2A is a cross sectional view showing an end region of the fastening member of FIG. 1A as seen through line 2A-2A.

As shown in FIG. 2A, in some embodiments, the fastening element 116 may comprise a plurality of engaging elements 202 and a base 204. The fastening element 116 can be joined to a base substrate 220 in the fastening element zone 114 via a first bonding agent 218. In some embodiments, the base 204 can have a thickness 210 of greater than about 0.1 mm. In some embodiments, the base 204 can have a thickness 210 of greater than or equal to about 0.15 mm. In some embodiments, the base 204 can have a thickness 210 of greater than or equal to about 0.2 mm.

An example of a suitable bonding agent for joining the fastening element 116 to the base substrate 220 is made from Bostik located in Wauwatosa, Wis., having a model number H2988-F02. In some embodiments, the fastening element 116 can be joined to the base substrate 220 via the first bonding agent plus mechanical bonds, fusion bonds, the like, or any combination thereof. In some embodiments, the fastening element 116 can be joined to the base substrate 220 via mechanical bonds, fusion bonds, or the like, or any suitable combination thereof.

Depending on the chemical makeup of the base 204, the thickness 210 to achieve the desired first stiffness, mentioned previously, can vary. However, one skilled in the art would be able to determine the thickness of the base 204 required to achieve the first stiffness based on the test methods provided herein.

Figure 2B:
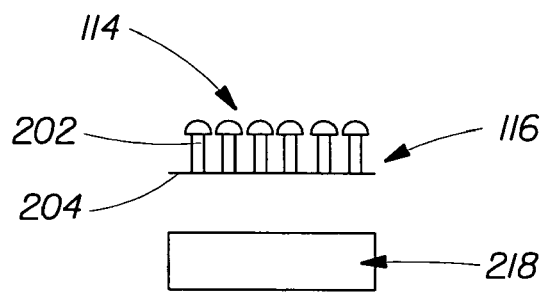
FIGS. 2B-2J are cross sectional views showing other embodiments for an end region of the fastening member of FIG. 1A.

As shown in FIG. 2B, in some embodiments, the stiffness in the fastening element zone 114 can be increased, in part, by the first bonding agent 218. The first bonding agent 218 can join the fastening element 116 to the base substrate 220 in the fastening element zone 114. A suitable amount of first bonding agent 218 can be applied to achieve the first stiffness. Exemplary basis weights of the first bonding agent 218 are discussed hereafter.

Figure 2C:
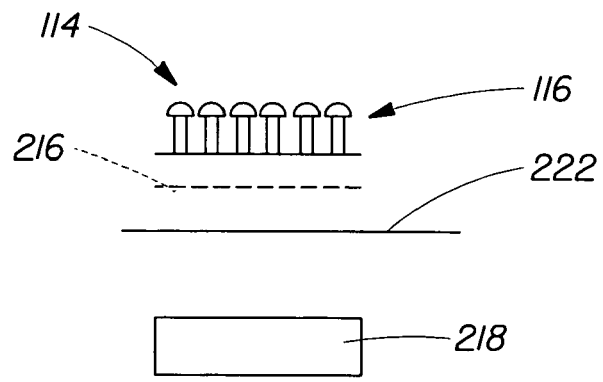

As shown in FIG. 2C, in some embodiments, the stiffness of the fastening element zone 114 can be increased in part, by the first bonding agent 218 and a first substrate 222. The fastening element 116 can be joined to the first substrate 222 via a second bonding agent 216. The first substrate 222 can be joined to the base substrate 220 via the first bonding agent 218. In some embodiments, the first bonding agent 218 and the second bonding agent 216 may comprise the same materials. In some embodiments, the first bonding agent 218 and the second bonding agent 216 may comprise different materials.

In some embodiments, the basis weight of the first bonding agent 218 and/or the second bonding agent 216 in the fastening element zone 114 can be greater than or equal to about 30 gsm. In other embodiments, the first bonding agent 218 and/or the second bonding agent 216 in the fastening element zone 114 can have a basis weight of greater than or equal to about 60 gsm. In some embodiments, the first bonding agent 218 and/or the second bonding agent 216 in the fastening element zone 114 can have a basis weight of greater than or equal to about 100 gsm. An example of a suitable bonding agent for joining the first substrate 222 to the base substrate 220 is made from Bostik located in Wauwatosa, Wis., having a model number H2511.

The first substrate 222 can be of any suitable width. For example, in some embodiments, the first substrate 222 can extend from the interface 1700 (shown in FIGS. 1A and 1B) to the outboard end 104 (shown in FIGS. 1A and 1B) of the fastening member 100 (shown in FIGS. 1A and 1B), thereby comprising the entire end region 120. In some embodiments, the first substrate 222 can be disposed within the fastening element zone 114 and can be disposed in a portion of the intermediate zone 112 and/or the grip zone 118. In other embodiments, the first substrate 222 can be disposed only in the fastening element zone 114.

Figure 2D:
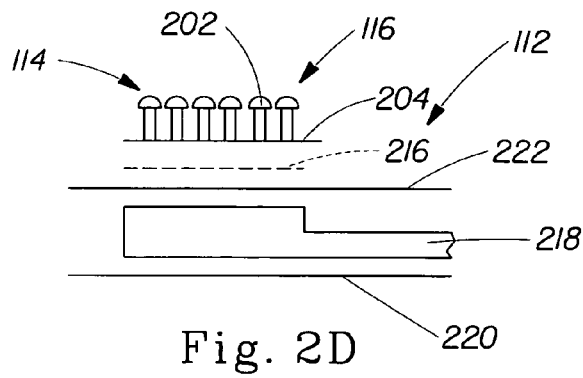
Figure 2E:
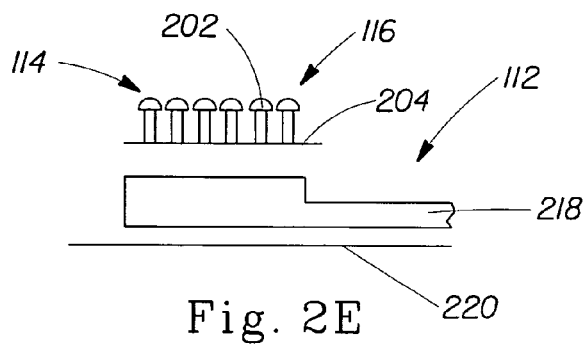

As shown in FIG. 2D-2E, in some embodiments, the first bonding agent 218 can have a varying basis weight from the fastening element zone 114 to the intermediate zone 112. As shown in FIG. 2D, in some embodiments, the first bonding agent 218 can be used to join the first substrate 222 to the base substrate 220. As shown in FIG. 2E, in some embodiments, the fastening element 116 can be joined to the base substrate 220 via the first bonding agent 218. As shown, the first bonding agent 218 can have a varying basis weights from the fastening element zone 114 to the intermediate zone 112, in some embodiments. For example, in some embodiments, the basis weight of the first bonding agent 218 in the fastening element zone 114 can be greater than the basis weight of the bonding agent 218 in the intermediate zone 112. In some embodiments, the basis weight of the first bonding agent 218 in the fastening element zone 114 can be greater than or equal to about 30 gsm. In other embodiments, the first bonding agent 218 in the fastening element zone 114 can have a basis weight of greater than or equal to about 60 gsm. In some embodiments, the first bonding agent 218 in the fastening element zone 114 can have a basis weight of greater than or equal to about 100 gsm.

In some embodiments, the basis weight of the first bonding agent 218 in the intermediate zone 112 can be less than about 30 gsm. In other embodiments, the first bonding agent 218 can have a basis weight of less than about 20 gsm in the intermediate zone 112. In other embodiments, a ratio of the basis weight of the first bonding agent 218 in the fastening element zone 114 to basis weight of the first bonding agent 218 in the intermediate zone 112 can be about 10:1. In other embodiments, the ratio can be about 5:1. In some embodiments, the ratio can be about 2:1. In other embodiments, the ratio can be about 1.5:1.

Also, as shown in FIGS. 2D-2E, the thickness of the first bonding agent 218 can vary from the fastening element zone 114 to the intermediate zone 112. For example, the thickness of the first bonding agent 218 in the fastening element zone 114 can be from about 0.02 mm to about 1 mm or any individual number within the range. The thickness of the first bonding agent 218 in the intermediate zone 112 can be from about 0.02 mm to about 0.08 mm or any individual number within the range. In some embodiments, the thickness of the first bonding agent 218 in the fastening element zone 114 can be greater than the thickness of the first bonding agent 218 in the intermediate zone 112.

In other embodiments, the increased stiffness in the fastening element zone 114 can be achieved by creating various areas of the first bonding agent 218. For example a first area of first bonding agent 218 can be disposed in the fastening element zone 114 while a second area of first bonding agent 218 can be disposed in the intermediate zone 112. In some embodiments, there can be gaps in between the adjacent areas of first bonding agent 218. In some embodiments, the increased stiffness can be achieved by varying the bonding agent utilized. For example, the first bonding agent 218 can be utilized in the fastening element zone 114 while the second bonding agent 216, having different properties than the first bonding agent 218, can be utilized in the intermediate zone 112.

Depending on the chemical makeup of the first bonding agent 218 and/or the second bonding agent 216, the amount of the first bonding agent 218 and/or the second bonding agent 216 which can achieve the desired first stiffness and/or second stiffness can vary. However, one skilled in the art would be able to determine the amount of the first bonding agent 218 and/or the second bonding agent 216 required to achieve the first stiffness based on the test methods provided herein.

In other embodiments, the increased stiffness can be achieved in the fastening element zone 114 via a variation in basis weight of the first substrate 222 and/or a variation in basis weight of the base substrate 220. For example, the basis weight of the first substrate 222 can be greater in the fastening element zone 114 compared to the basis weight of the first substrate 222 in the intermediate zone 112. Similarly, the basis weight of the base substrate 220 can vary. The basis weights of the individual substrate layers are discussed hereafter.

Varying the basis weights of the first substrate 222 and/or the base substrate 220 can occur via any suitable process known in the art. For example, the amount of material in portions of the first substrate 222 and/or the base substrate 220 can vary such that an increased basis weight occurs in those portions. Other suitable examples of increasing the basis weight of the first substrate 222 and/or the base substrate 220 are discussed with regard to FIGS. 2F-2I. For the sake of explanation, the discussion is limited to the base substrate 220; however, the first substrate 222 can be similarly configured.

Figure 2F:
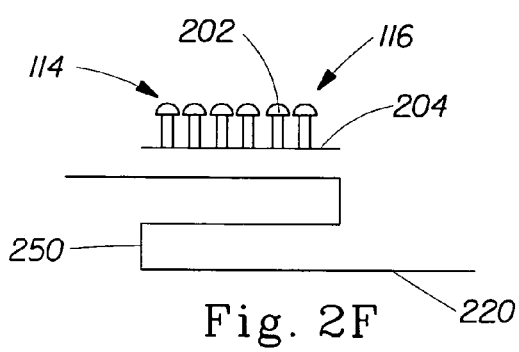
Figure 2G:
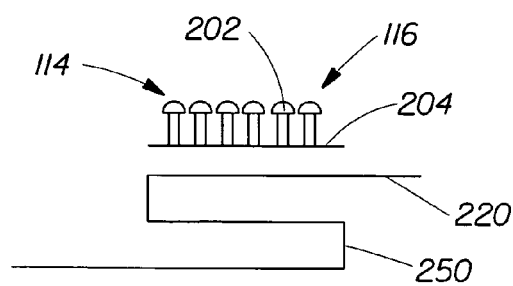
Figure 2H:
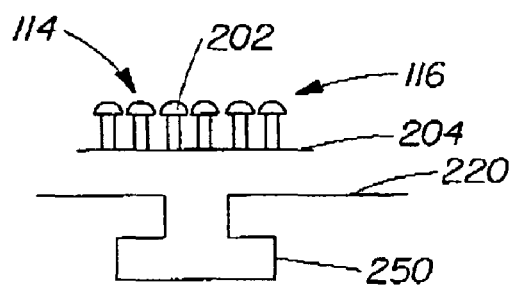
Figure 2I:
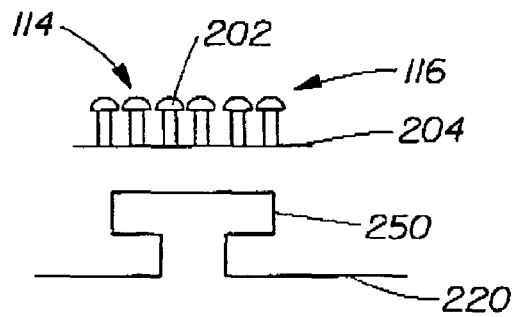

As shown in FIGS. 2F-2I, in some embodiments, the increased stiffness in the fastening element zone 114 can be achieved by folding the base substrate 220. For example, the base substrate 220 can be folded such that a folded portion 250 of the base substrate 220 is disposed within the fastening element zone 114. As shown in FIG. 2F, a Z-fold can be utilized, in some embodiments. In some embodiments, as shown in FIG. 2G, a reverse Z-fold can be utilized. In some embodiments, as shown in FIGS. 2H and 2I, a double Z-fold can be utilized. As shown in FIG. 2H, in some embodiments, the folded portion 250 can be disposed on the base substrate 220 opposite the fastening element 116. As shown in FIG. 2I, in some embodiments, the folded portion can be disposed on the base substrate 220 proximate to the fastening element 116.

Folding the base substrate 220 can increase the thickness of the fastening member in the fastening element zone 114 and can increase the basis weight of base substrate 220 in the fastening element zone 114. The folded portions 250 can be held in place by any suitable means. Some examples of suitable means for holding the folded portions 250 in place include, adhesive, mechanical bonds, fusion bonds, the like, and suitable combinations thereof.

Figure 2J:
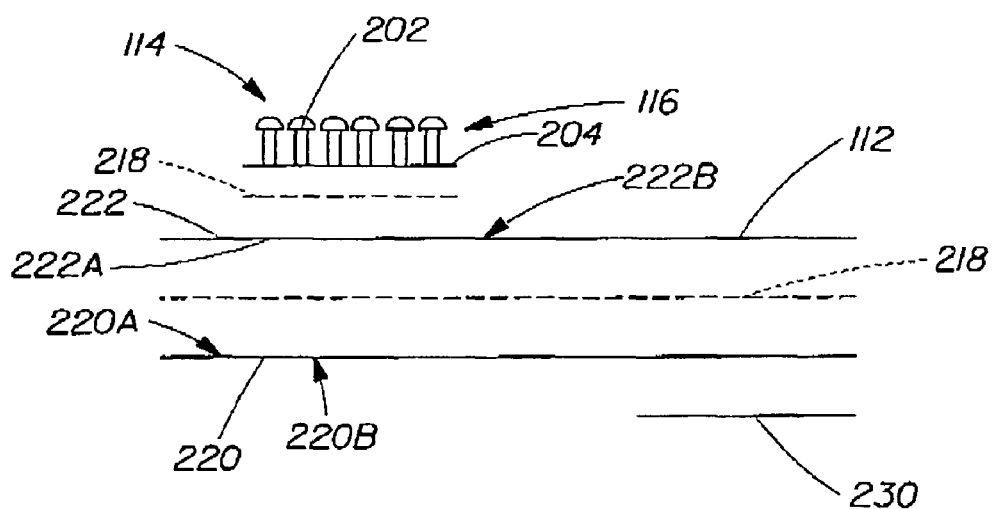

As shown in FIG. 2J, in some embodiments a stiffening material 230 having suitable stiffness may be added to the end region 120 over part of all on the intermediate region 112 to achieve the desired stiffness in the fastening element zone 114. In some embodiments, the stiffening material 230 can be a web which extends the full width of the end region 120 or a portion of the width as shown. In some embodiments, the stiffening material 230 can be disposed in the intermediate zone 112. In some embodiments, the stiffening material 230 can be disposed in the fastening element zone 114.

In some embodiments, the stiffening material 230 can be disposed on an exterior surface 222B of the first substrate 222. In some embodiments, the stiffening material 230 can be disposed on an exterior surface 220B of the base substrate 220. In some embodiments, the stiffening material 230 can be disposed on an interior surface 222A of the first substrate 222. In some embodiments, the stiffening material 230 can be disposed on an interior surface 220A of the base substrate 220. In some embodiments, although not shown, multiple stiffening materials can be disposed in any combination of locations described above.

Any suitable combination of the above means for increasing the stiffness in the fastening element zone 114 described in regard to FIGS. 2A-2J can be used to increase the stiffness of the fastening element zone 114.

The end region 120 of the fastening member 100 can be associated with the panel region 110 in a number of different configurations. For example, as discussed previously, the fastening element 116 can be joined to the base substrate via the bonding agent. In other embodiments, the first substrate 222 can be disposed between the fastening element 116 and the base substrate 220. Other exemplary configurations of the end region 120 and the panel region 110 are provided with regard to FIGS. 3A-3D. For the sake of explanation, each of the end regions 120 in the embodiments shown in FIGS. 3A-3D comprises the first substrate 222. However, as heretofore discussed, the end region 120, in some embodiments, may be configured without the first substrate 222.

As shown in FIG. 3A, in some embodiments, the panel region 110 may comprise the base substrate 220 while the end region 120 comprises the first substrate 222 and a portion of the base substrate 220. A portion of the first substrate 222 can overlap the base substrate 220 and can be joined to the base substrate 220 by the first bonding agent 218. As shown, in some embodiments, the base substrate 220 can overlap a portion of the first substrate 222 in the end region 120.

The first bonding agent 218 can extend in a direction generally parallel to the second direction 491 inward from an outer edge 312 to an inner edge 310 of the first bonding agent 218. The interface 1700 between the panel region 110 and the end region 120 can be disposed at the inner edge 310 of the first bonding agent 218.

In some embodiments, the base substrate 220 can extend to the outer edge 312 of the first bonding agent 218. In some embodiments, the outer edge 312 of the first bonding agent 218 can be disposed within the intermediate zone 112. In some embodiments, the first substrate 222 can extend laterally inward from about the outboard end 104 of the fastening member 100 to about the inner edge 310 of the first bonding agent 218.

Figure 3C:
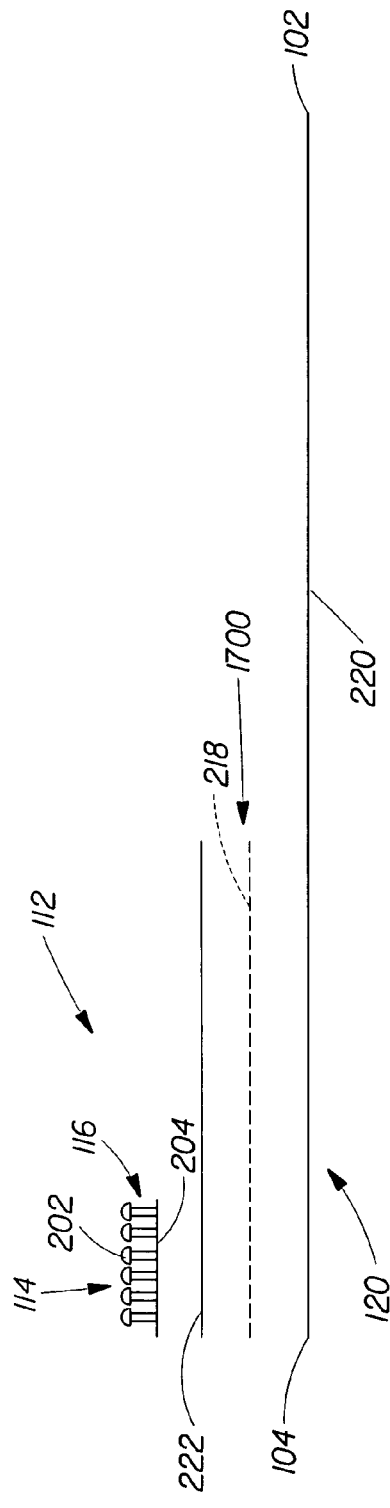

As shown in FIG. 3B, in some embodiments, the base substrate 220 can overlap a portion of the end region 120 such that the fastening element zone 114 comprises a portion of the base substrate 220. As shown in FIG. 3C, in some embodiments, the base substrate 220 may extend from the inboard end 102 of the fastening member 100 outward to the outboard end 104 such that the base substrate 220 comprises the entire end region 120.

Figure 3D:
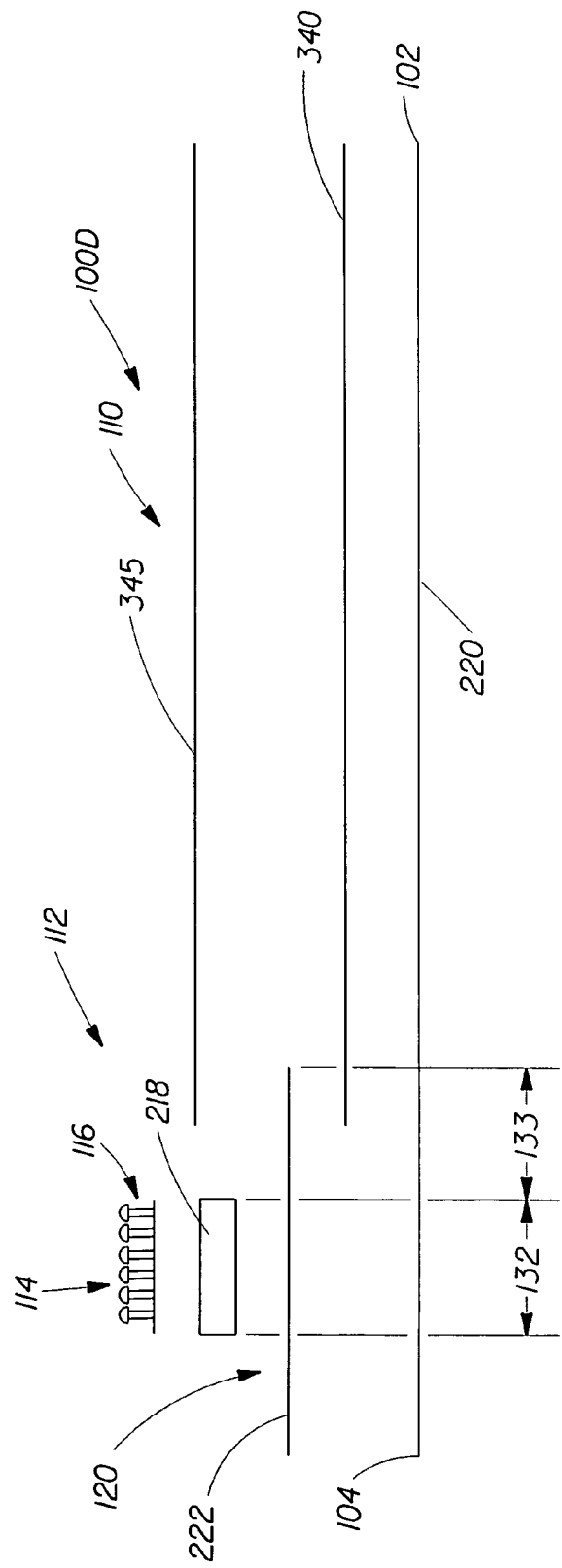

As shown in FIG. 3D, in some embodiments, the panel region 110 and/or the end region 120 may comprise laminated structures. As shown, in some embodiments, the panel region 110 may comprise the base substrate 220, an elastomeric element 340, and a cover substrate 345. The elastomeric element 340 can be joined to the base substrate 220 in a face-to-face orientation. Similarly, the cover substrate 345 can be joined to the elastomeric element 340 in a face-to-face orientation.

As shown, in some embodiments, the base substrate 220 can extend from the inboard end 102 to the outboard end 104 of a fastening member 100D. In some embodiments, the elastomeric element 340 can extend from the inboard end 102 outward such that the intermediate zone 112 comprises a portion of the elastomeric element 340. In some embodiments, the elastomeric element 340 can extend from the inboard end 102 to the outboard end 104 such that the elastomeric element 340 comprises the entire end region 120. In some embodiments, the elastomeric element 340 can be disposed in the panel region 110 and in a portion of the fastening element zone 114 and the intermediate zone 112.

The cover substrate 345 can extend outward from the inboard end 102 of the fastening member 100D such that the intermediate zone 112 comprises a portion of the cover substrate 345, in some embodiments. In some embodiments, the cover substrate 345 may extend from the inboard end 102 to the outboard end 104 such that the cover substrate 345 comprises the entire end region 120. In other embodiments, the cover substrate 345 can be disposed in the panel region 110 and in a portion of the fastening element zone 114 and the intermediate zone 112.

As mentioned above, the end region 120 may also comprise a laminated structure. For example, in some embodiments, the end region 120 may comprise the base substrate 220, the first substrate 222, the first bonding agent 218, and the fastening element 116. In some embodiments, the first substrate 222 can extend inward from the outboard end 104 of the fastening member 100D such that a portion of the first substrate 222 overlaps the elastomeric element 340 and/or the cover substrate 345. As shown, in some embodiments, the first substrate 222 can be disposed between the cover substrate 345 and the elastomeric element 340. In other embodiments, the first substrate 222 can be disposed between the elastomeric element 340 and the base substrate 220. In other embodiments, the first substrate 222 can be disposed on the cover substrate 345 such that the first substrate 222 is not disposed between the cover substrate 345 and the elastomeric element 340. In other embodiments, the first substrate 222 can be disposed on an outer surface of the base substrate 220.

As shown, in some embodiments, the first bonding agent 218 can be disposed on a face of the base substrate 220. In some embodiments, the fastening element 116 can be joined to the base substrate 220 via the first bonding agent 218. The bonding agent can be between any layers adjacent each other in the overlapped areas.

The base substrate 220, the first substrate 222, and/or the cover substrate 345, may comprise a woven, nonwoven, film, a laminate, the like, or any combination thereof. Additionally, the base substrate 220, the first substrate 222, and/or the cover substrate 345, may be extensible and/or elastically extensible. Where the base substrate 220, the first substrate 222, and/or the cover substrate 345 comprise a nonwoven, any suitable nonwoven can be used. In some embodiments, the nonwoven may comprise one layer of fibers. In other embodiments, the nonwoven may comprise more than one layer of fibers. Any suitable nonwoven can be used. For example, a suitable nonwoven may comprise fibers made of polypropylene, polyethylene, polyester, nylon, cellulose, polyamide, or combinations of such materials. Fibers of one material or fibers of different materials or material combinations may be used in the first and/or second nonwoven. Exemplary nonwoven materials include spunbond, spunbond meltblown spunbond (SMS), spunbond meltblown spunbond (SMMS), carded, meltblown, and the like. Particularly acceptable nonwovens include high elongation carded (HEC) nonwovens and deep activation polypropylene (DAPP) nonwovens. Any process known in the art may be used to make the nonwovens.

The nonwoven may comprise fibers that are bonded mechanically, including fibers that are needle punched or hydro entangled. Other suitable bonding processes for producing a suitable nonwoven for use in the present invention are spun bonding, thermally bonding, bonding by various types of chemical bonding such as latex bonding, powder bonding, and the like.

In certain embodiments, the basis weight of the nonwoven can be in the range of about 10 gsm to about 100 gsm or any individual number within the range. In other embodiments, the basis weight of the nonwoven can be in a range of about 40 gsm to about 80 gsm. In yet other embodiments, the basis weight of the nonwoven can be in a range of about 50 gsm to about 60 gsm. The basis weights of the substrates of the present invention can be any suitable basis weight.

The fibers may be of any suitable size and shape. In some embodiments, the fiber may have a denier ranging from about 1 to about 10 or any individual number within the range. In some embodiments, the denier of the fibers can range from about 1 to about 8. In other embodiments, the denier of the fibers can range from about 1 to about 5.

The elastomeric element 340 may comprise any suitable elastic known in the art. Suitable elastomeric elements may comprise a wide variety of materials as are well known in the art include elastomeric films, polyurethane films, elastomeric foams, formed elastic scrim, and synthetic elastomers (e.g., Lycra™). For example, an elastomeric element of the present invention may include elastic strands or elastic films. Any suitable elastic film known in the art can be used. Suitable elastic films may comprise polypropylene, polyethylene, polyolefins, styrene-isoprene-styrene, styrene-butadiene-styrene, or combinations thereof. In some embodiments, the basis weight of the films can range from about 10 gsm to about 100 gsm or any individual number within the range.

Alternatively, or in conjunction with the elastic film, the elastomeric element 340 may further comprise elastic strands. Suitable elastic strands can be made of a resilient elastic thermoplastic material. The elastic strands may be made from liquid elastic that is extruded through a die to achieve the desired strand elastic diameter and/or shape. The shape of the extruded elastic strands is not limited. For example, typical elastic strands have a circular cross sectional shape, but sometimes the elastic strands may have different shapes, such as a trilobal shape, or a flat (i.e., "ribbon" like) shape. Suitable elastic strand shapes include rectangles, circles, ellipses, diamonds, triangles, parallelograms, trapezoids, wedges, or other sections of circles or ellipses, other polygons, or other irregular enclosed shapes. Furthermore, the thickness or diameter of the elastic strands may vary in order to accommodate a particular application. In some embodiments, the thickness of elastic strands may be in the range of about 0.02 mm to about 1 mm or any individual number within the range. In some embodiments, the basis weight is in the range of about 20 g/m2 to about 300 g/m2 or any individual number within the range. The elastic strands may be applied separately to the substrate, can be extruded onto the substrate, or can be printed onto the substrate.

Suitable apparatuses and methods for printing elastomeric elements in any orientation are described in U.S. Application Publication No. 2004/0181200; U.S. Application Publication No. 2004/0193133; and WO 2005/110731 A3. For the printing of elastic strands, the individual elastic strands may be configured as lines or strands generally having widths less than about 2 mm and typically less than about 1 mm. Linear elastic strands may be configured as bands generally having widths between about 2 mm and about 20 mm and aspect ratios ranging from about 2:1 to about 100:1. Typically, the thickness of an elastic strand may be in the range of about 0.02 mm to about 5 mm and the basis weight is in the range of about 20 g/m$^2$ to about 300 g/m$^2$.

The first bonding agent 218 and the second bonding agent 216 may comprise any suitable bonding agent known in the art. For example, in some embodiments, the first bonding agent 218 and/or the second bonding agent 216 may comprise an adhesive. Any suitable adhesive can be used in the present invention. For example, the adhesive may comprise styrene-olefin-styrene triblock copolymers such as styrene-isoprene-styrene, styrene-butadiene-styrene, or combinations thereof.

In some embodiments, the first bonding agent 218 and/or the second bonding agent 216 may comprise a polymer. Any suitable polymer known in the art can be utilized. Some examples of suitable polymers include a high modulus hot melt polymer or may include a molten polymer. Any suitable molten polymer can be used. Some examples of molten polymers include polyethylene, polypropylene, the like, or any suitable combinations thereof.

The stiffening material 230 can be any suitable stiffening material known in the art. Some examples of suitable stiffening materials 230 include webs of any type, e.g. woven, nonwoven, laminates, natural or synthetic materials including polypropylene, polyethylene, poly(ethylene terephthalate), nylon, paper, cellulose, styrene-isoprene-styrene, styrene-butadiene-styrene block copolymers, the like, or any suitable combination thereof. Some examples of suitable laminates include bilaminates of film and nonwoven such as M18-750 or M18-1018 manufactured by Clopay Corporation, Cincinnati, Ohio. An example of a suitable nonwoven is Typar SBPP3301Y manufactured by BBA Fiberweb™, located in Brentwood, Tenn.

The stiffening material 230 may comprise portions of other elements. For example, the stiffening material 230 may comprise a portion of the base substrate 220. In another example, the stiffening material 230 may comprise a portion of the first substrate 222. The stiffening material 230 can be configured similarly to the base substrate 220 and/or the first substrate 222.

In some embodiments, the stiffening material 230 can be printed onto the base substrate 220, the first substrate 222, the cover substrate 345, and/or the elastomeric element 340. In some embodiments where the stiffening material comprises a thermoplastic, the materials and processes for printing thermoplastics are described in WO 2003/039426 A2 and in WO 2004/082918.

Web of Fastening Members:

The fastening members described heretofore can be produced on a web of material. In certain embodiments, a number of fastening members can be produced on a parent web. For example, some parent webs may include up to eight fasteners on a single web. Embodiments where parent webs comprise more than eight fastening members on a single web or less than eight fastening members on a single web are contemplated. Configurations of fastening members on a parent web of material are discussed hereafter with regard to FIGS. 4A-4D.

For the purposes of the present invention, a parent web comprises a web of material having a plurality of fastening members thereon. Adjacent fastening members are disposed on the web both in a machine direction and in a cross machine direction. Parent webs can be separated along parent separation boundaries thereby creating a plurality of fastening member webs.

The fastening member webs can be one of two types of web. First, for example where the fastening member web comprises a single panel region and a single end region, the fastening member web is a single repeating unit web. Second, for example, where a fastening member web comprises at least one end region, at least one panel region, and at least one shared region which may comprise either a panel region or an end region, the fastening member web is a siamese web. Where the fastening member web is a siamese web, the siamese web can further be separated along one or more siamese separation boundaries thereby creating a plurality of single repeating unit webs. The single repeating unit web comprises a plurality of fastening elements with adjacent fastening elements being disposed in the machine direction.

Figure 4A:
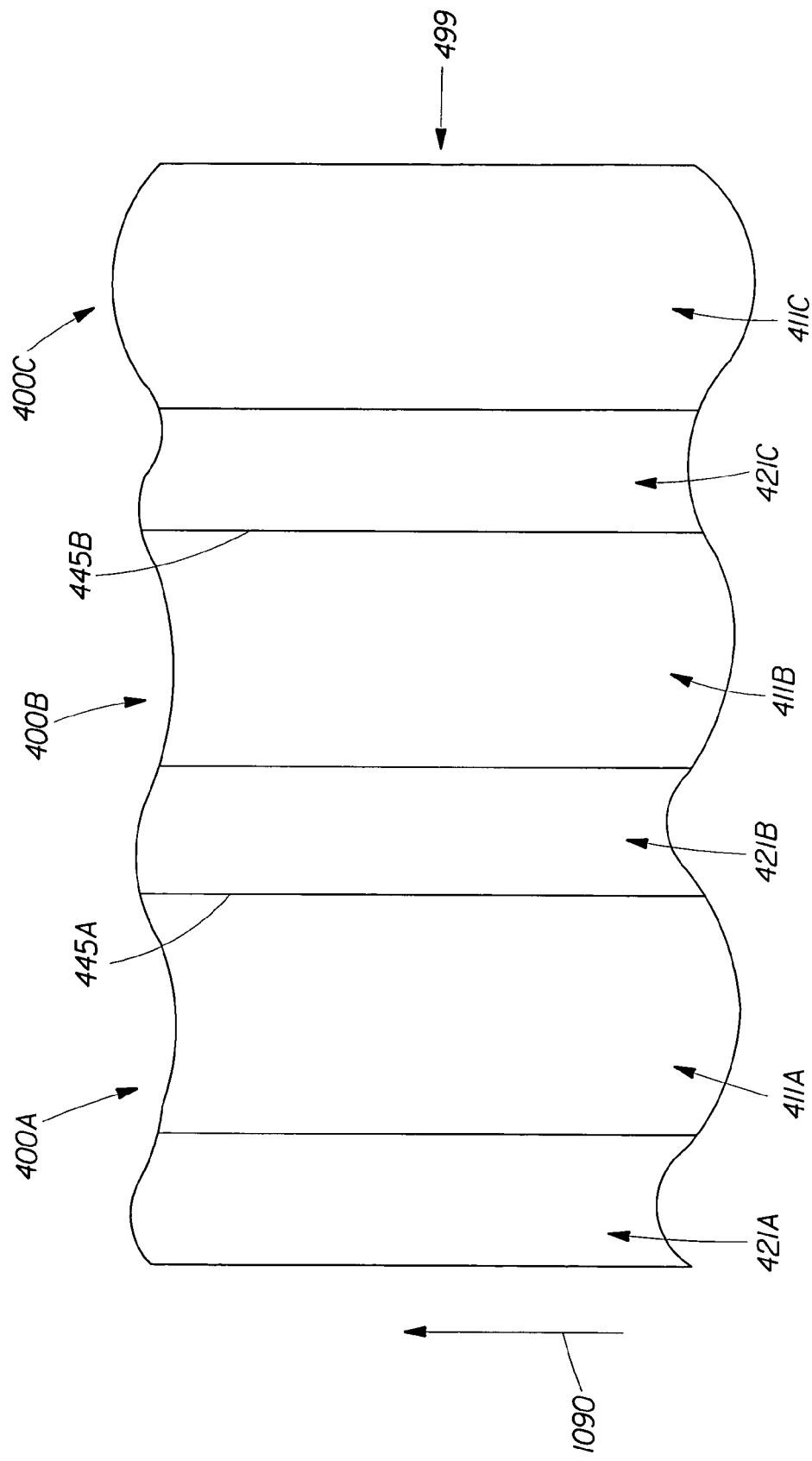
FIGS. 4A-4E are plan views showing embodiments for sections of parent webs comprising fastening members constructed in accordance with the present invention.

As shown in FIG. 4A, in some embodiments, a plurality of fastening members can be included on a parent web 499. As shown, in some embodiments, the parent web 499 may comprise a first panel area 411A, a second panel area 411B, and a third panel area 411C. Also, the parent web 499 may comprise a first end area 421A, a second end area 421B, and a third end area 421C.

In some embodiments, the parent web 499 can be separated along parent separation boundaries 445A and 445B to create three single repeating unit webs. Additionally, by separating the parent web 499 along the parent separation boundaries 445A and 445B, the first panel area 411A and the first end area 421A can comprise a first fastening member 400A. Similarly, a second fastening member 400B can comprise the panel area 411B and the end area 421B while a third fastening member 400C comprises the panel area 411C and 421C. As shown, in some embodiments, the parent separation boundaries can be generally parallel to a machine direction 1090.

Figure 4B:
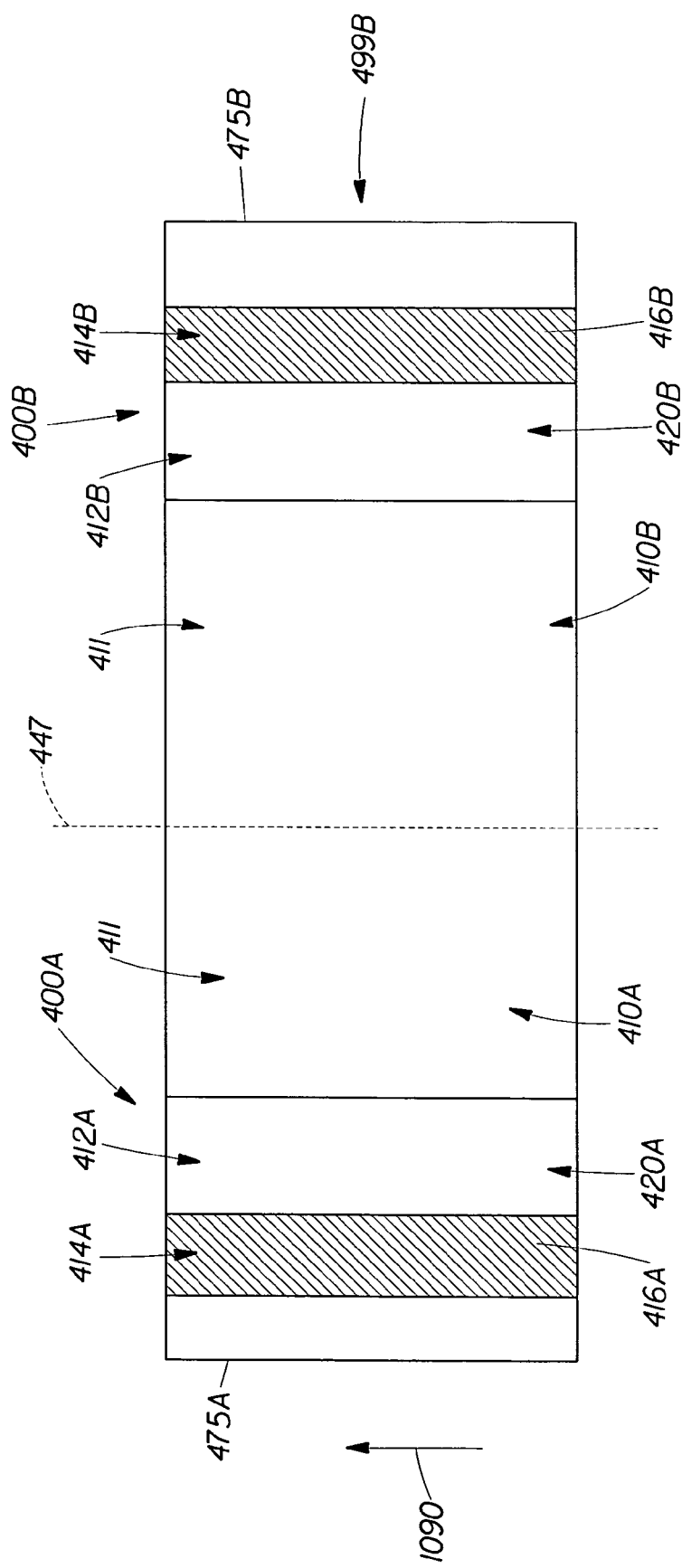

As shown in FIG. 4B, a siamese web 499B may comprise a plurality of fastening members, e.g. 400A and 400B. As shown, in some embodiments, the fastening members 400A and 400B can be configured such that the fastening member 400A and 400B share a panel area 411. Because the panel regions 410A and 410B share a common panel area 411, in some embodiments, the fastening member 400A can be separated from the fastening member 400B. In some embodiments, the separation process can involve cutting the siamese web 499B along a siamese separation boundary 447 which can extend through the panel area 411 generally parallel to the machine direction 1090. By separating the siamese web 499B along the siamese separation boundary 447, two single repeating unit webs can be created.

Each of the fastening members 400A and 400B may comprise a first end region 420A and a second end region 420B, respectively, and each may comprise a panel region 410A and 410B, respectively. In some embodiments, the first end region 420A can be disposed adjacent to a first longitudinal edge 475A of the siamese web 499B, and the second end region 420B can be disposed adjacent to a second longitudinal edge 475B of the siamese web 499B. The panel area 411 can be disposed between the first end region 420A and the second end region 420B. Also, as shown, in some embodiments, fastening element 416A and 416B can be joined to the end regions 420A and 420B, respectively, either prior to or after any separation process.

The fastening elements 416A and 416B can define a first fastening element zone 414A and a second fastening element zone 414B, respectively. A first intermediate zone 412A can be disposed between the first fastening element zone 414A and the panel area 411. Similarly, a second intermediate zone 412B can be disposed between the second fastening element zone 414B and the panel area 411. Embodiments comprising a plurality of fastening elements are contemplated.

Figure 4C:
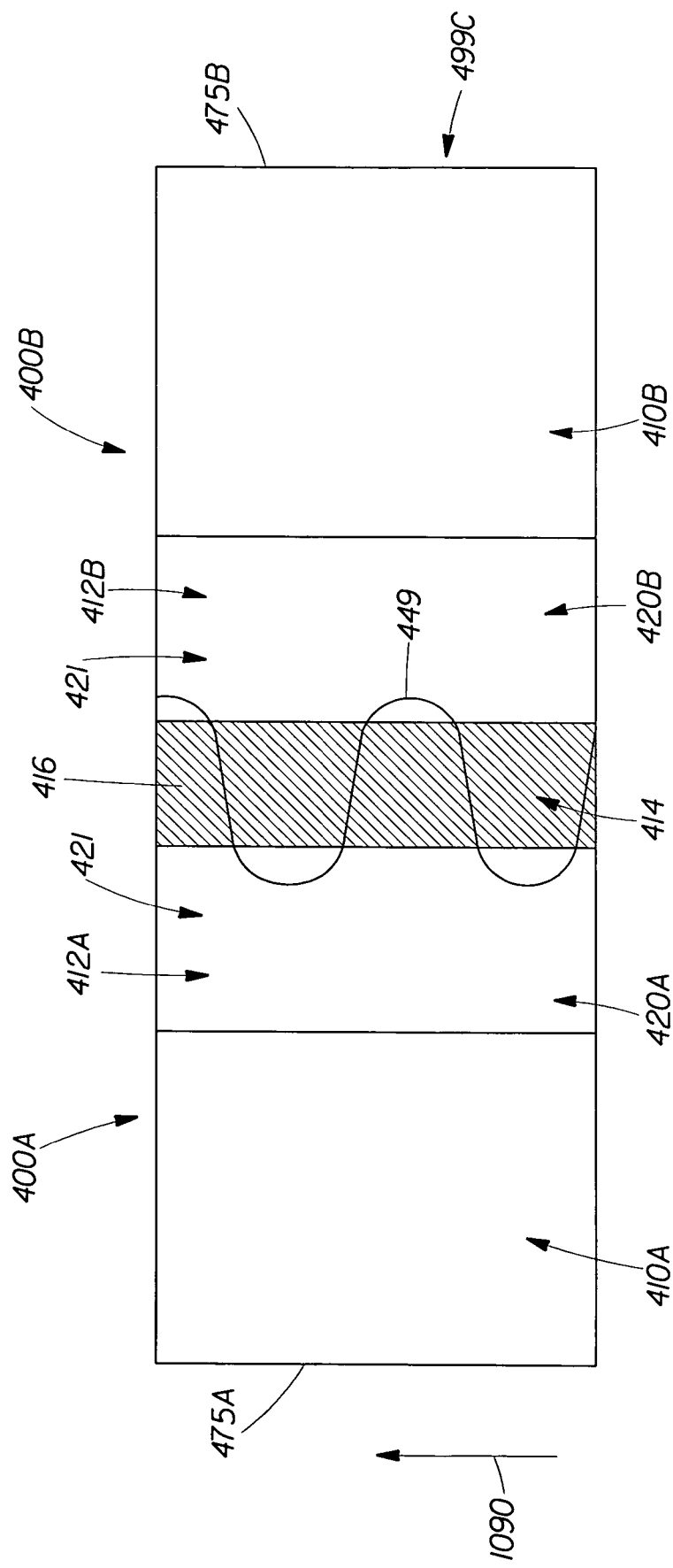

As shown in FIG. 4C, in some embodiments, the first fastening member 400A and the second fastening member 400B can be disposed on a siamese web 499C such that they share a common end area 421. The first fastening member 400A and the second fastening member 400B can be separated, in some embodiments, by separating the end area 421 along a siamese separation boundary 449. By separating the siamese web 499C along the siamese separation boundary 449, two single repeating unit webs can be created. Note that in some embodiments, a fastening element 416 can be joined to the end area 421 prior to the separation of the first fastening member 400A and the second fastening member 400B. In other embodiments, the fastening element 416 can be joined to the end are 421 after the separation of the first fastening member 400A and the second fastening member 400B.

As shown, in some embodiments, the first panel region 410A can be disposed adjacent to the first longitudinal edge 475A, and the second panel region 410B can be disposed adjacent to the second longitudinal edge 475B. The end area 421 can be disposed between the first panel region 410A and the second panel region 410B. The fastening element 416 can define a fastening element zone 414.

In some embodiments, the first intermediate zone 412A can be disposed between the first panel region 410A and the fastening element zone 414. Similarly, in some embodiments, the second intermediate zone 412B can be disposed between the second panel region 410B and the fastening element zone 414.

The first intermediate zone 412A and the second intermediate zone 412B can be configured similarly to the intermediate zone 112 discussed heretofore. Similarly, the first fastening element zone 414A and the second fastening element zone 414B can be configured similarly to the fastening element zone 114 discussed heretofore. The panel area 411 and the end area 421 can be configured similarly to the panel regions and the end regions discussed heretofore.

Embodiments comprising a plurality of fastening elements are contemplated. Exemplary embodiments comprising a plurality of fastening elements are discussed with regard to FIGS. 5A-5B.

Figure 4D:
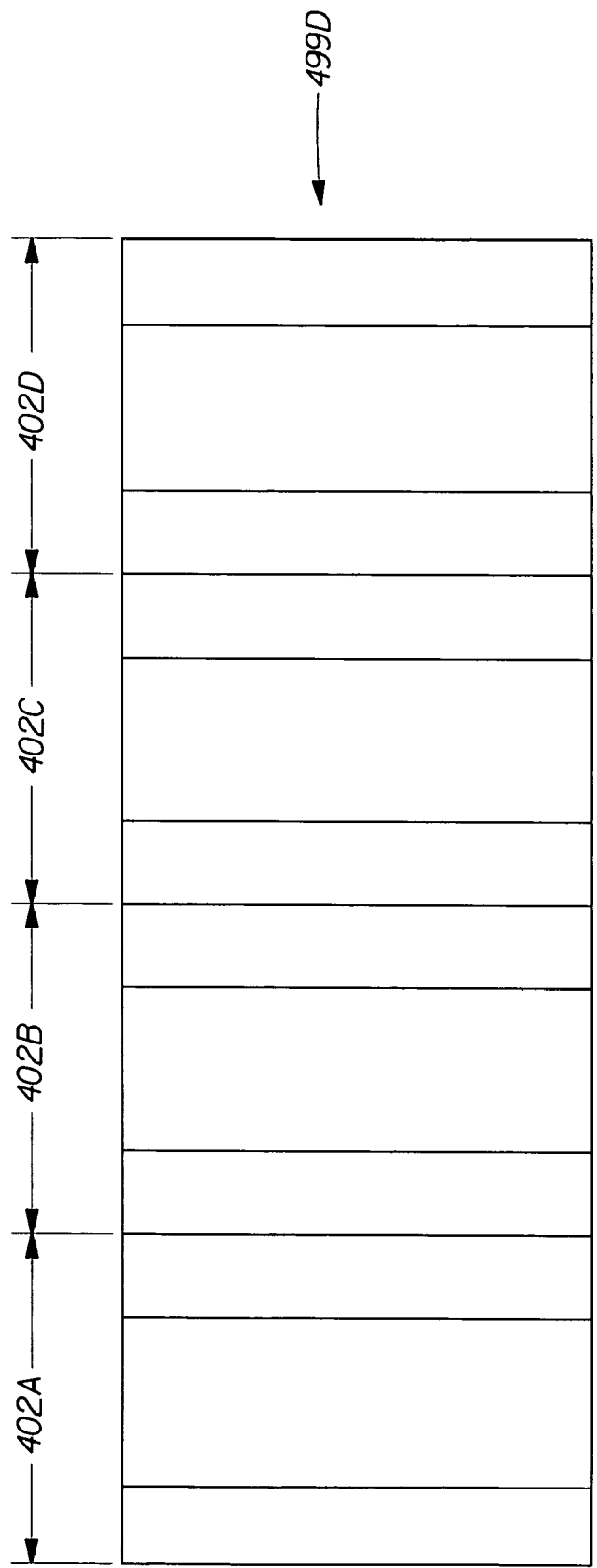
Figure 4E:
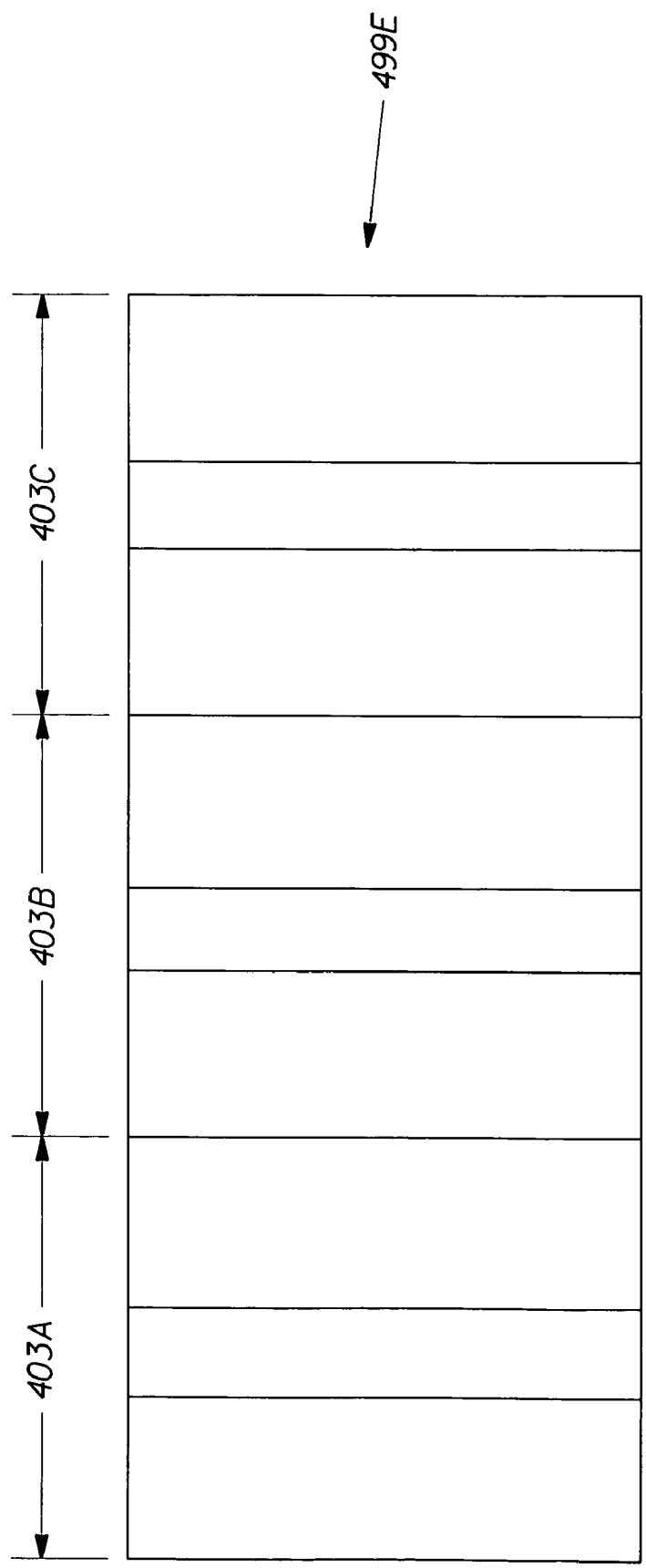

As shown in FIG. 4D, in some embodiments, a parent web 499D may comprise a plurality of siamese webs. As shown the siamese webs 402A, 402B, 402C, and 402D, may be configured similar to the siamese web 499B (shown in FIG. 4B), in some embodiments. As shown in FIG. 4E, in some embodiments, a parent web 499E may comprise a plurality of siamese webs 403A, 403B, and 403C. In some embodiments, the siamese webs 403A, 403B, and 403C, may be configured similar to the siamese web 499C (shown in FIG. 4C). In some embodiments, any suitable combination of siamese webs may be utilized in a parent web.

Any of the parent webs, fastening member webs, siamese webs, and/or single repeating unit webs, described herein can be rolled up and stored or rolled up and sold as rollstock goods. Alternatively, the parent webs, fastening member webs, siamese webs, and/or single repeating unit webs, can be placed in a box and sold as boxed goods. Alternatively, the parent webs, fastening member webs, siamese webs, and/or single repeating unit webs, can be packaged in any suitable form and sold as packaged goods.

Alternatively, the parent webs, fastening member webs, siamese webs, and/or single repeating unit webs, may be processed and converted on line. Specifically, the parent webs, fastening member webs, siamese webs, and/or single repeating unit webs, can be manufactured and converted into portions of a consumer goods in a converting process directly after manufacture of the parent web, fastening member web, siamese web, and/or single repeating unit webs.

Additionally, although FIGS. 4A-4C depict fastening members having only one fastening element 416, embodiments are contemplated wherein each fastening member has a plurality of fastening elements. Examples of such embodiments are discussed further with regard to FIGS. 5A-5B.

Figure 5A:
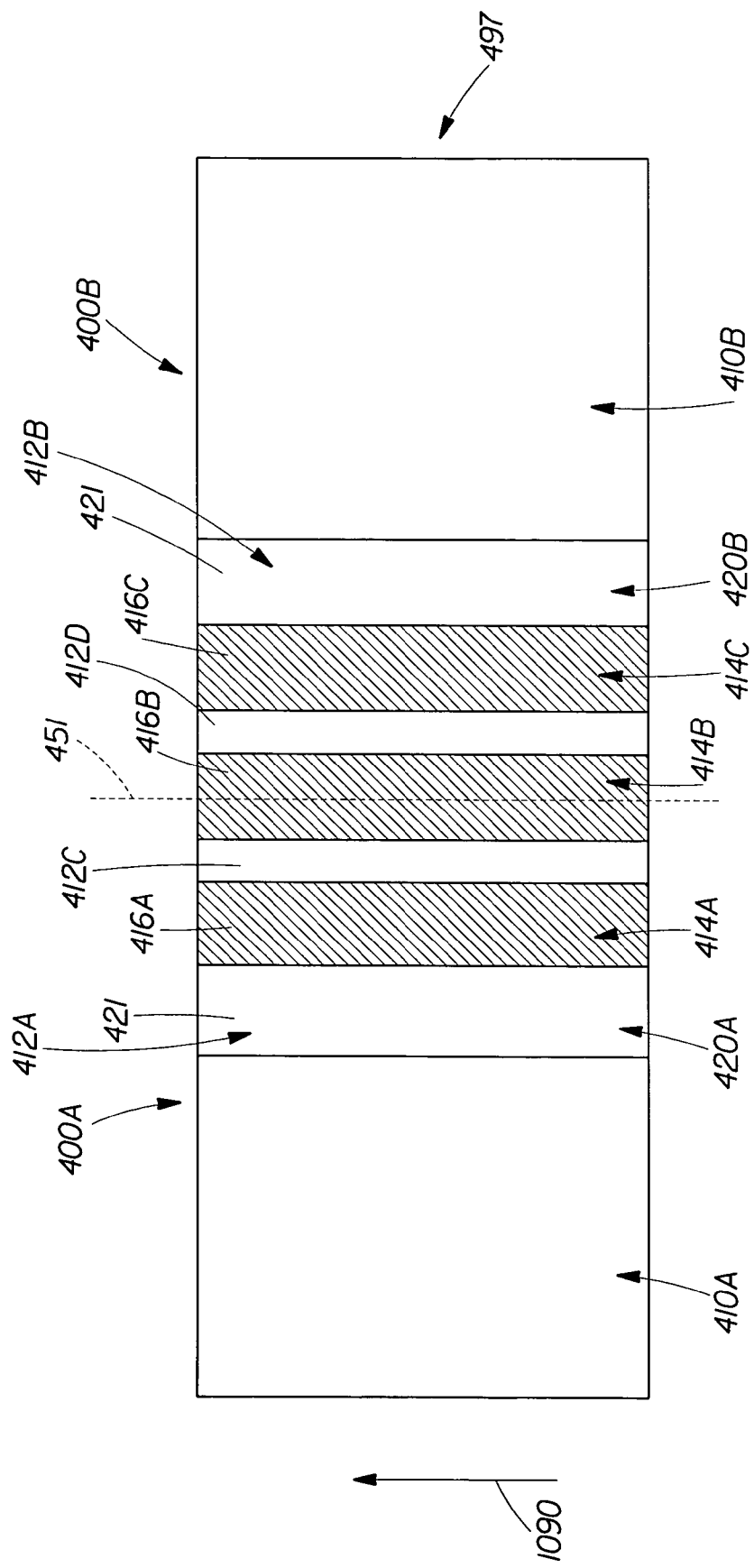
FIGS. 5A-5B are plan views showing embodiments for sections of parent web comprising fastening members constructed in accordance with the present invention.

As shown in FIG. 5A, in some embodiments, a plurality of fastening elements 416A, 416B, and 416C, can be disposed within the end area 421. The first fastening element 416A can define the first fastening element zone 414A, the second fastening element 416B can define the second fastening element zone 414B, and the third fastening element 416C can define a third fastening element zone 414C. The fastening element zones can be configured similarly to those fastening element zones discussed heretofore. In some embodiments, the first fastening element zone 414A, the second fastening element zone 414B, and the third fastening element zone 414C may comprise stiffnesses which are about equal. In some embodiments, at least one of the first fastening element zone 414A, the second fastening element zone 414B, or the third fastening element zone 414C may comprise a stiffness which is unequal to the stiffness of the remaining fastening element zones.

Similarly, in some embodiments, the first fastening element 416A, the second fastening element 416B, and the third fastening element 416C, may comprise the same type of fastening mechanism, e.g. engaging component, receiving component, adhesive, cohesive, the like. In some embodiments, at least one of the first fastening element 416A, the second fastening element 416B, or the third fastening element 416C, may comprise a different fastening mechanism than the other two. For example, one fastening element may comprise an engaging component, one fastening element may comprise a receiving component, and the remaining fastening element may comprise an adhesive. Any suitable combination of fastening elements may be utilized.

In some embodiments, the first intermediate zone 412A can be disposed between the first fastening element 416A and the first panel region 410A, and the second intermediate zone 412B can be disposed between the third fastening element 416C and the second panel region 410B. In some embodiments, third and fourth intermediate zones 412C and 412D can be disposed between the first fastening element 416A and the second fastening element 416B and between the second fastening element 416B and the third fastening element 416C, respectively. The intermediate zones can be configured similarly to those intermediate zones discussed heretofore.

Alternatively, in some embodiments, the first fastening element 416A, the second fastening element 416B and the third fastening element 416C, can define a single fastening element zone 414. In this embodiment, no intermediate zones would be disposed between the first fastening element 416A and the second fastening element 416B or between the second fastening element 416B and the third fastening element 416C.

As shown, in some embodiments, the first fastening member 400A and the second fastening member 400B can be separated along a siamese separation boundary 451 which splits the siamese web 497 down the middle. As shown, in some embodiments, the siamese separation line 451 can run generally parallel to the machine direction 1090. In some embodiments, the siamese separation boundary 451 can cut through the second fastening element 416B such that the first fastening member 400A and the second fastening member 400B each comprise a portion of the second fastening element 416B.

Figure 5B:
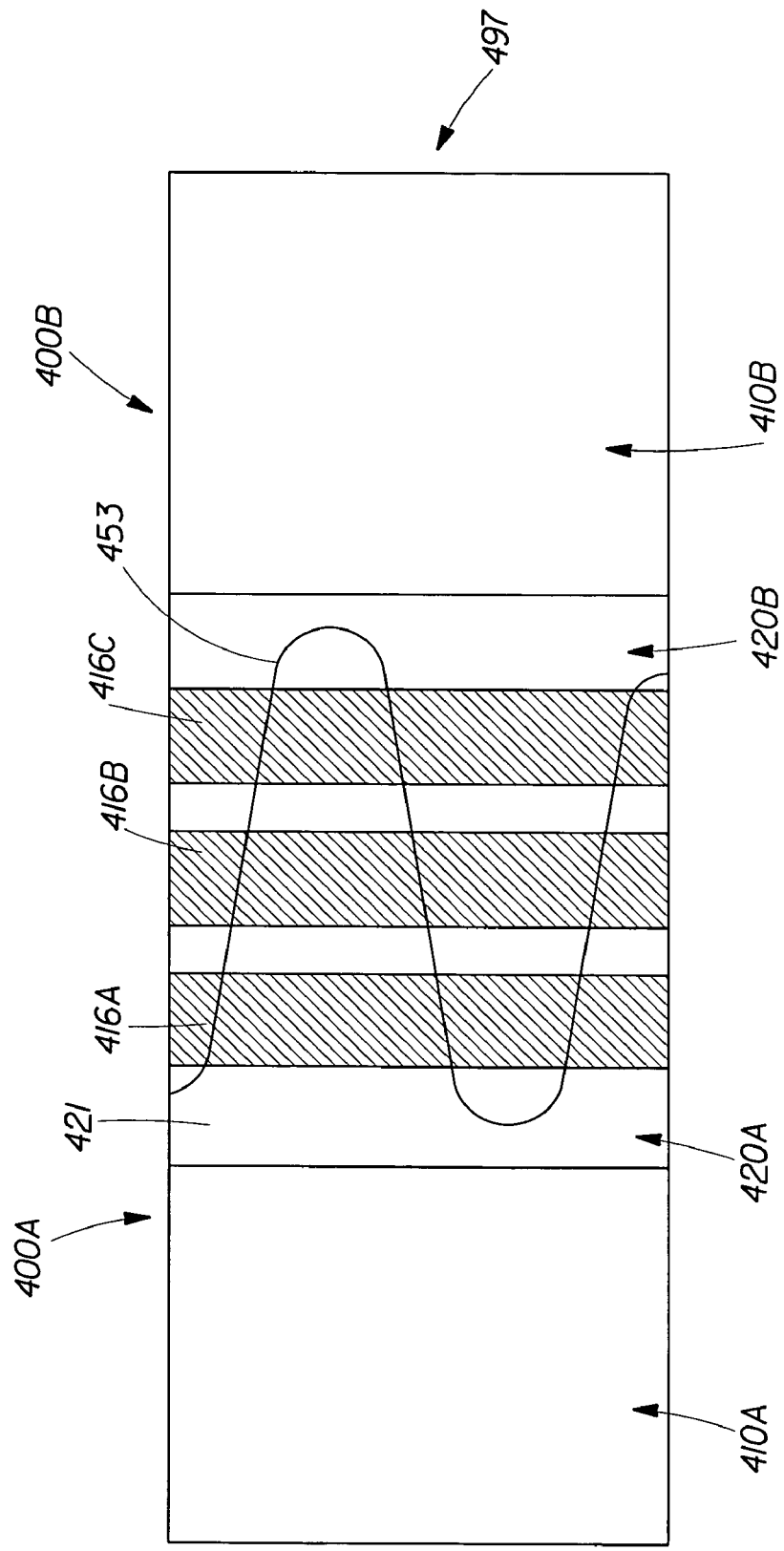

Alternatively, as shown in FIG. 5B, in some embodiments, a siamese separation boundary 453 can extend across one or more of the fastening elements 416A, 416B, and/or 416C. In some embodiments, the siamese separation boundary 453 can extend into the first panel region 410A and/or the second panel region 410B. Alternatively, in some embodiments, the siamese separation boundary 453 can be completely contained within the end area 421.

As shown in FIGS. 4A, 4B, and 5A, the parent separation boundaries 445, 445A, 445B, and/or the siamese separation boundary 451, may comprise a straight line and be generally parallel to the machine direction 1090. However, as shown in FIGS. 4C and 5B, the parent separation boundary and/or the siamese separation boundary may not be limited in the path which it may follow. For example, as shown in FIGS. 4C and 5B, in some embodiments, the siamese separation boundary 447 and/or 453 may comprise a sinusoidal shape. The parent separation boundaries can be similarly configured.

Regardless of the number of fastening elements disposed in an end region or end area, the parent separation boundaries and/or the siamese separation boundaries may comprise any suitable shape known in the art. Some examples of suitable shapes include sinusoidal, curvilinear, arcuate, rectilinear, square wave, serrated, the like, or any combination thereof. In some embodiments, a siamese separation boundary and/or a parent separation boundary may comprise a plurality of separation lines. An example of such an embodiment is discussed with regard to FIG. 6.

Figure 6:
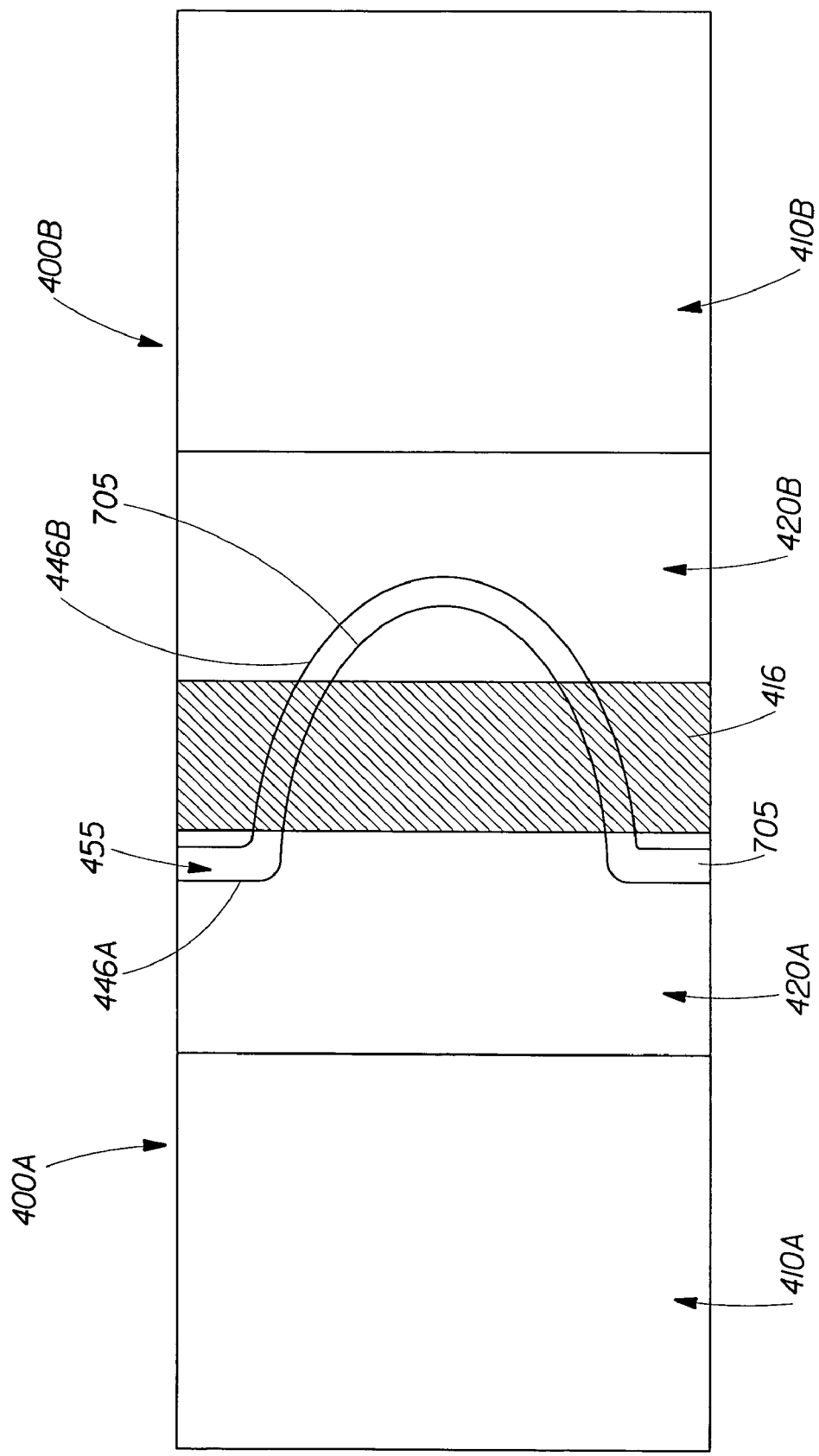
FIG. 6 is a plan view showing an embodiment for a cut line used for separating fastening members on a parent web, thereby creating a fastening member web.

As shown in FIG. 6, the siamese separation boundary 455 may comprise a plurality of separation lines 446A and 446B, for example. Utilizing the separation lines 446A and 446B to separate the first fastening member 400A from the second fastening member 400B can create a trim piece 705, in some embodiments.

While the trim piece 705 can be considered wasted material, an advantage of utilizing the separation lines 446A and 446B is that the first end region 420A and the second end region 420B can be shaped. Additionally, utilization of more than one separation line can allow more flexibility in the shapes which can be created when compared to single separation lines, e.g. see FIG. 5B). For example, a single separation line can create shaped end regions which are symmetrical. In contrast, the separation lines 446A and 446B can shape end regions of the fastening members 400A and/or 400B such that the end regions are not necessarily symmetrical.

Shaped end regions on fastening members can provide an aesthetic quality to the fastening member. In some embodiments, the fastening members can be shaped even further after an initial separation process.

As discussed in regard to FIG. 4A, in some embodiments, the parent web 499 can be along the parent separation boundary 445A and a parent separation boundary 445B to create three fastening member webs. Referring to FIG. 6, similarly, by separating the first fastening member 400A and the second fastening member 400B along siamese separation boundary 455, two separate single repeating unit webs can be created.

Figure 7:
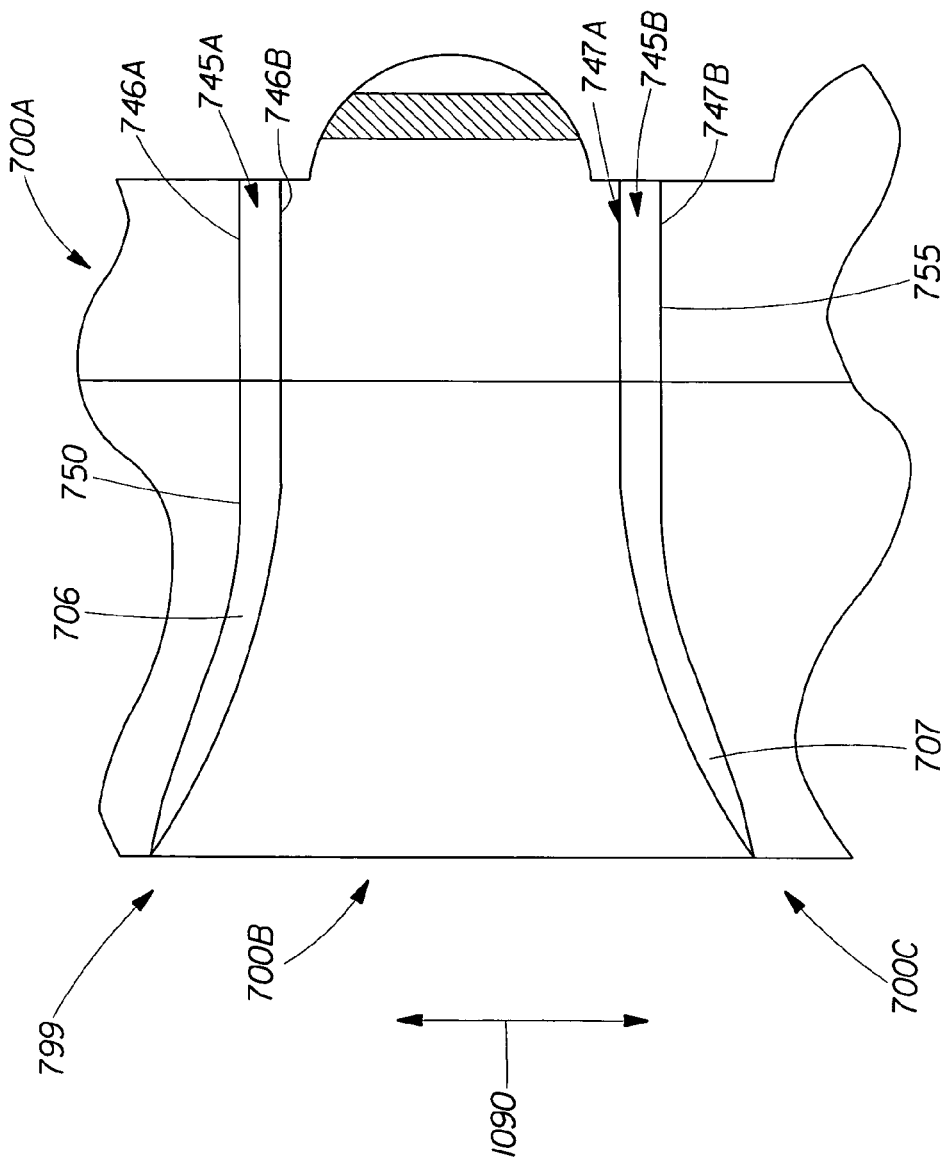
FIG. 7 is a plan view showing the fastening member web created by the separation in FIG. 6.

As shown in FIG. 7, a single repeating unit web 799 is shown comprising a plurality of fastening members, 700A, 700B, and 700C. In addition to the separation process which creates separate single repeating unit webs, another separation process can occur, in some embodiments. In some embodiments, the other separation process can be utilized to remove individual fastening members, 700A, 700B, and 700C, from the single repeating unit web 799. For example, as shown in some embodiments, the single repeating unit web 799 can be separated along a leading edge 750 and a trailing edge 755, thereby freeing the fastening member 700B from the single repeating unit web 799.

Fastening member separation boundaries 745A and 745B can extend along the leading edge 750 and trailing edge 755, respectively. In some embodiments, the fastening member separation boundary 745A may comprise a plurality of separation lines 746A and 746B. The plurality of separation lines 746A and 746B can create a trim piece 706. Similarly, the fastening member separation boundary 745B may comprise, in some embodiments, a plurality of separation lines 747A and 747B. The plurality of separation lines 747A and 747B can create a trim piece 707. Embodiments are contemplated where the fastening member separation boundaries 745A and/or 745B comprise single cut lines.

The separation of the fastening member 700B from the single repeating unit web 799 may comprise two separation steps. For example, the separation along the leading edge 750 may occur prior to the separation along the trailing edge 755. Alternatively, in some embodiments, the separation along the trailing edge 755 can occur prior to the separation along the leading edge 750. In other embodiments, the separation of the leading edge 750 and the trailing edge 755 may occur contemporaneously.

The process of separating a web along parent separation boundaries, e.g. 445, 445A, 445B, and/or siamese separation boundaries, e.g. 447, 449, 451, 453, can shape a portion of an end region, in some embodiments. In some embodiments, separating a web along the parent separation boundaries, e.g. 445, 445A, 445B, and/or siamese separation boundaries, e.g. 447, 449, 451, 453, can shape a portion of the end region and/or a portion of the panel region. Similarly, the process of separating a web along fastening member separation boundaries 745A and 745B, in some embodiments, can shape a portion of a panel region and/or shape a portion of the end region.

Similar to the separation boundaries discussed above, the fastening member separation boundaries 745A and 745B may comprise any suitable shape known in the art. Some examples of suitable shapes include sinusoidal, curvilinear, arcuate, rectilinear, square wave, serrated, the like, or any combination thereof.

The separation process mentioned heretofore may be accomplished by any suitable means known in the art. Some examples of suitable means include cutting, via a knife roll and anvil roll, for example; water jet, laser cutting, the like, or any suitable combinations thereof.

As discussed previously, the separation of a web along the parent separation boundary, the siamese separation boundary, and/or the fastening member separation boundary, can free fastening members from their respective webs. Subsequently, in some embodiments, the fastening members can be attached to disposable absorbent articles adjacent to their inboard ends 102 (shown in FIGS. 1A and 1B).

Figure 8A:
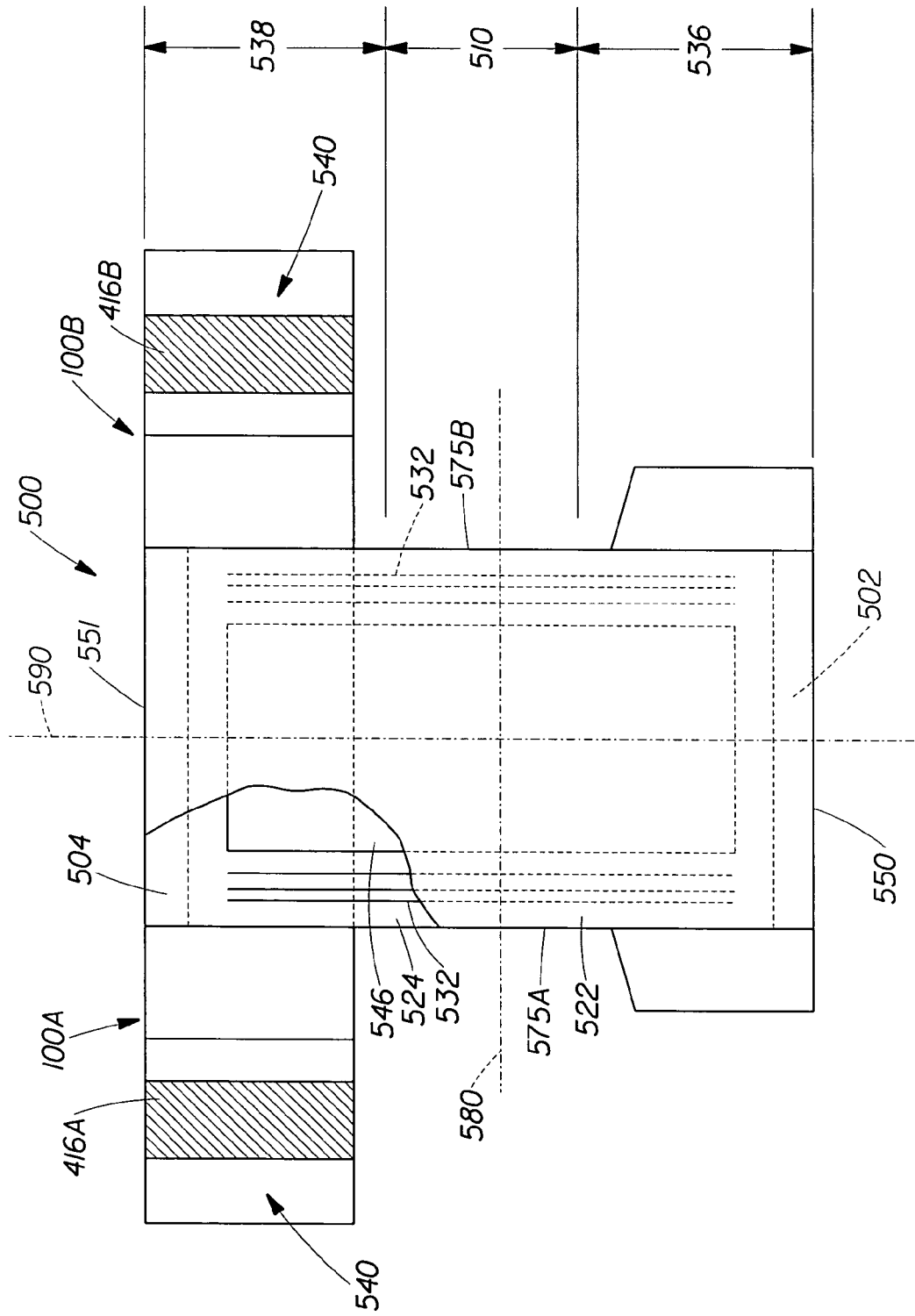
FIG. 8A is a plan view showing a disposable absorbent article having fastening members constructed in accordance with the present invention.

For example, as shown in FIG. 8A, fastening members 100A and 100B can be joined to a disposable absorbent article 500. As shown, in some embodiments, the fastening member 100A can be joined to the disposable absorbent article 500 adjacent to a first longitudinal edge 575A of the disposable absorbent article 500. Similarly, in some embodiments, the fastening member 100B can be joined to the disposable absorbent article 500 adjacent a second longitudinal edge 575B of the disposable absorbent article 500.

As shown in FIG. 8A, the disposable absorbent article 500 may further comprise a liquid pervious topsheet 522 and a backsheet 524 joined to at least a portion of the topsheet 522. The disposable absorbent article 500 further comprises an absorbent core 546 positioned between the topsheet 522 and the backsheet 524. The disposable absorbent article 500 may further comprise the belt 528, elastic leg features 532, a first waist member 502 and a second waist member 504.

A portion of the periphery of the disposable absorbent article 500 can be defined by the longitudinal edges 575A and 575B; a first waist edge 550, and the second waist edge 551. The longitudinal edges 575A and 575B can run generally parallel to a longitudinal centerline 590 of the disposable absorbent article 500. The first waist edge 550 and the second waist edge 551 can run generally parallel to a lateral centerline 580 of the disposable absorbent article 500.

The first waist member 502 and/or the second waist member 504 can be elastically extensible. As shown, in some embodiments, the first waist member 502 can be disposed adjacent the first waist edge 550. In some embodiments, the second waist member 504 can be disposed adjacent to the second waist edge 551. Generally, the first waist member 502 and/or the second waist member 504 can be under tension prior to being joined to the disposable absorbent article 500. So, upon release of at least a portion of the tension applied to the first waist member 502 and/or the second waist member 504, a portion of the disposable absorbent article 500 joined thereto can corrugate. This corrugation of the disposable absorbent article 500 can allow the first waist member 502 and/or the second waist member 504 and the disposable absorbent article 500 to expand and contract about the waist of a wearer, thereby providing more comfort and improved fit to a wearer. Examples of suitable waist members 502 and/or 504 include those described in U.S. Pat. Nos. 4,515,595; 5,151,092; and 5,221,274. Although disposable diapers are generally constructed so as to have two elastic waist features, one positioned in a first waist region and one positioned in a second waist region, diapers can be constructed with a single elastic waist feature.

The disposable absorbent article 500 may further comprise outer cuffs and inner cuffs to improve containment of liquids and other body exudates. Each elasticized outer cuff may include several different embodiments for reducing the leakage of body exudates in the leg regions. Outer cuffs and inner cuffs are further described in U.S. Pat. Nos. 3,860,003; 4,909,803; and 4,695,278.

In some embodiments, the fastening members 100A and 100B can form a portion of the leg openings when the disposable absorbent article 500 is fastened. The fastening members 100A and 100B can form a portion of the leg openings which would be disposed on an outer surface of a leg of a wearer. A crotch region 510 of the disposable absorbent article 500 in conjunction with the first waist region 536 and the second waist region 538 can form a portion of the leg openings which would be disposed on an inner surface of the leg of the wearer.

In some embodiments, the fastening members 100A and 100B can be joined to an outer-facing surface of the backsheet 524. In some embodiments, the fastening members 100A and 100B can be joined to a wearer-facing surface of the topsheet 522. In some embodiments, the fastening members 100A and 100B can be joined to the disposable absorbent article 500 between the topsheet 522 and the backsheet 524. The fastening members 100A and 100B can be joined to the disposable absorbent article 500 in any suitable configuration or location.

The disposable absorbent article 500 further comprises a fastening system 540 which joins at least a portion of a first waist region 536 with at least a portion of a second waist region 538, preferably to form leg and waist openings. The fastening system 540 also works with the waist members(s) 502 and/or 504 to maintain lateral tension in order to keep the disposable absorbent article 500 in place about the waist of the wearer. The fastening system 540 may comprise fastening elements 416A and 416B which, in some embodiments, can be disposed on the fastening members 100A and 100B. The fastening system 540 may further comprise a receiving component which, in some embodiments, is disposed in the first waist region 536 of the disposable absorbent article. The fastening element 416A and 416B can be configured to engage the receiving component thereby joining the first waist region 536 and the second waist region 538 of the disposable absorbent article 500.

In contrast, the separation of a web thereby creating individual fastening members is an optional step. Some examples of embodiments where the separation of a web thereby creating individual fastening members can be skipped are shown in FIGS. 8B and 9.

Figure 8B:
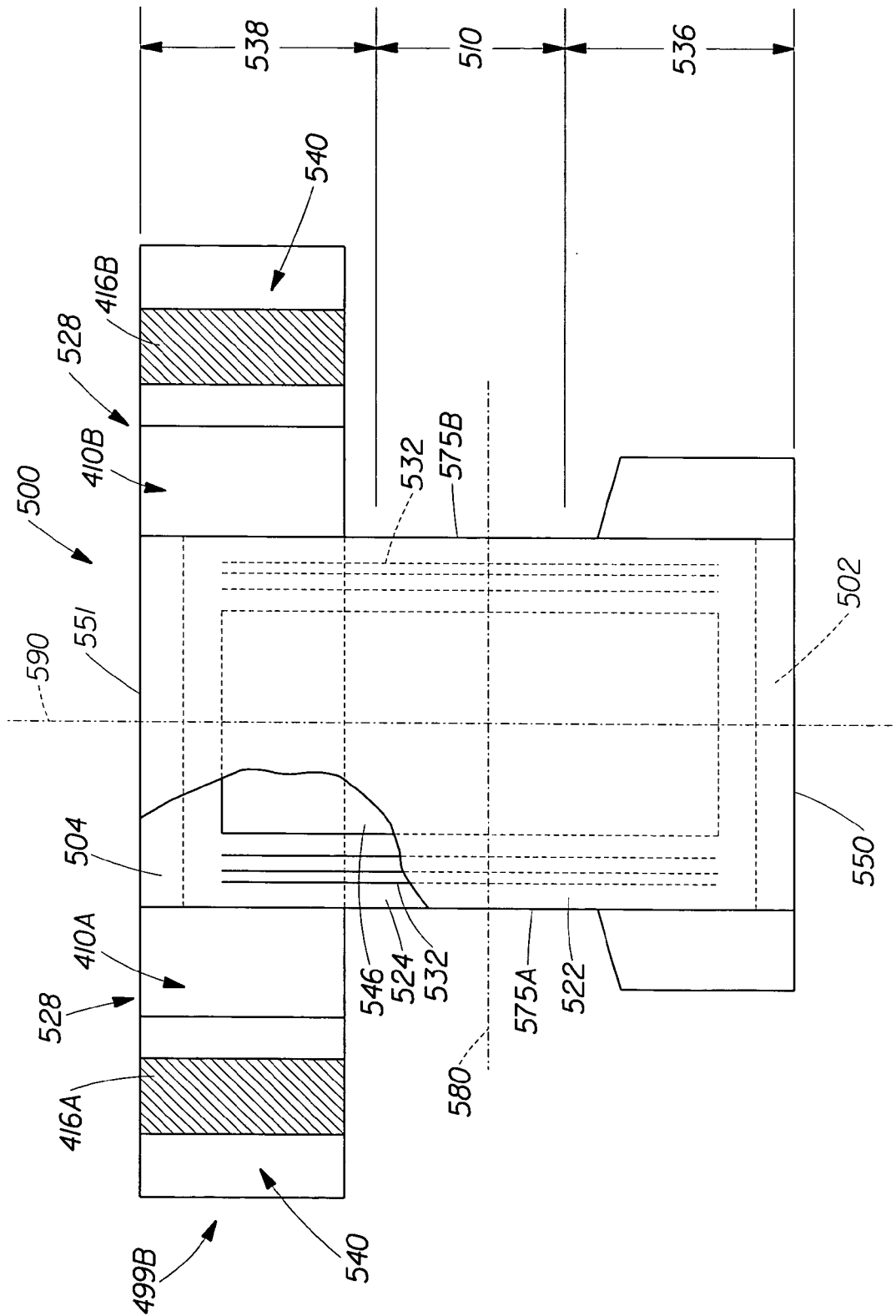
FIG. 8B is a plan view showing another embodiment for a disposable absorbent article having a belt constructed in accordance with the present invention.

As shown in FIG. 8B, in some embodiments, the siamese web 499B can be joined to the disposable absorbent article 500 as a belt 528. The belt 528 can be joined to the disposable absorbent article 500 such that a portion of the panel region 410A and a portion of the panel region 410B can extend outward from the first longitudinal edge 575A and the second longitudinal edge 575B of the disposable absorbent article 500, respectively. In some embodiments, the belt 528 can be joined to the disposable absorbent article 500 in a second waist region 538, and in some embodiments, the belt 528 can be joined to the disposable absorbent article 500 in a first waist region 536.

Alternatively, in some embodiments, the disposable absorbent article 500 may comprise a belt in the second waist region 538 and a belt disposed in the first waist region 536. In these embodiments, at least one of the belts in the first waist region and/or the belt in the second waist region comprise complimentary fastening elements. For example, the belt in the second waist region may include fastening elements which comprise engaging components while the belt in the first waist region may include fastening elements which comprise receiving components. Any suitable combination of complementary fastening elements can be used.

Figure 8C:
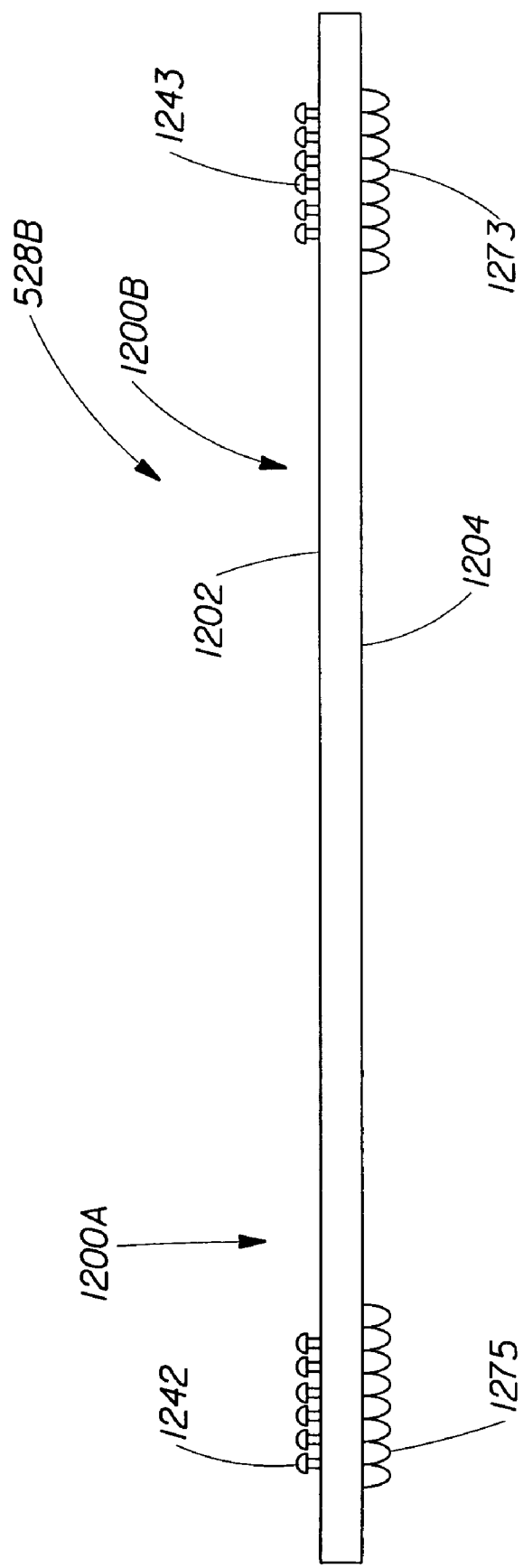
FIG. 8C is a plan view showing another embodiment for the belt of FIG. 8B.

In some embodiments, the disposable absorbent article 500 may comprise a belt having a plurality of fastening members as shown in FIG. 8C. As shown, in some embodiments, a belt 528B may comprise a plurality of fastening members 1200A and 1200B. Each of the fastening members 1200A and 1200B can include a plurality of fastening elements. For example, fastening member 1200A can include an engaging component 1242 having a plurality of engaging elements. The engaging component 1242 can be disposed on a first surface 1202 of the belt 528B. The fastening member 1200A may further comprise a receiving component 1275 which can be disposed on a second surface 1204 of the belt 528B, in some embodiments. The second surface 1204 can be opposite to the first surface 1202.

Similarly, the second fastening member 1200B may comprise an engaging component 1243 disposed on the first surface 1202 and an engaging component 1273 disposed on the second surface 1204, in some embodiments. One advantage of this arrangement is that the engaging components 1242 and 1243 can engage a receiving component disposed on the disposable absorbent article 500 (shown in FIG. 8A) or can join to the receiving components 1275 and 1273 on the belt 528B. For example, in some embodiments the engaging component 1242 can join the receiving component 1273 when fastened. In other embodiments, the engaging component 1243 can join the receiving component 1275 when fastened. Any of the fastening members discussed herein can be configured similarly to the fastening members 1200A and 1200B.

The fastening members 100A and 100B can be similarly configured to the belt 528 and/or belt 528B. In some embodiments, the fastening elements 100A and 100B, the belt 528, or the belt 528B can be prefastened and packaged as a preassembled article. In some embodiments, the fastening elements 100A and 100B, the belt 528, or the belt 528B, can be unassembled and packaged as an unassembled article.

Disposable absorbent articles may comprise many components, elements, members, etc. and can be constructed in a variety of manners. For example, the topsheet and the backsheet can have length and width dimensions generally larger than those of the absorbent core. The topsheet and the backsheet can extend beyond the edges of the absorbent core, thereby forming the periphery of the disposable absorbent article. The topsheet, the backsheet, and the absorbent core may include many different materials and may be assembled in a variety of well known configurations, exemplary diaper materials and configurations are described generally in U.S. Pat. Nos. 3,860,003; 5,151,092; and 5,221,274.

Any topsheet compatible with the present invention which is known in the art can be used in the present invention. A suitable material for a topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. As an example, a material suitable for use in a topsheet comprises a web of staple-length polypropylene fibers is manufactured by Veratec, Inc., a Division of International Paper Company, of Walpole, Mass. under the designation P-8.

Some examples of suitable topsheets are described further in U.S. Pat. Nos. 3,929,135; 4,324,246; 4,342,314; 4,463,045; 5,006,394; 4,609,518; 4,629,643. Any portion of the topsheet may be coated with a lotion as is known in the art. Examples of suitable lotions include those described in U.S. Pat. Nos. 5,607,760; 5,609,587; 5,635,191; 5,643,588; 5,968,025; 6,716,441; and PCT Publication No. WO 95/24173.

Further, the topsheet may be fully or partially elastically extensible or may be foreshortened so as to provide a void space between the topsheet and the absorbent core. Exemplary structures including elasticized or foreshortened topsheets are described in more detail in U.S. Pat. Nos. 4,892,536; 4,990,147; 5,037,416; and 5,269,775.

A suitable backsheet for use in the disposable absorbent article of the present invention may comprise a laminated structure. For example, the backsheet may comprise a first backsheet layer and a second backsheet layer. The second backsheet layer can be impervious to liquids (e.g., urine) and comprise a thin plastic film such as a thermoplastic film having a thickness, for example, of about 0.012 mm (0.5 mils) to about 0.051 mm (2.0 mils). Suitable backsheet films include those manufactured by Tredegar Corporation, based in Richmond, Va., and sold under the trade name CPC2 film. Either the first backsheet layer and/or the second backsheet layer may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. Nos. 5,938,648; 5,865,823; and 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Suitable exemplary absorbent structures for use as the absorbent core are described in U.S. Pat. Nos. 4,610,678; 4,673,402; 4,834,735; 4,888,231; 5,137,537; 5,147,345; 5,342,338; 5,260,345; 5,387,207; and 5,625,222.

The backsheet may be joined to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. Nos. 4,573,986; 3,911,173; 4,785,996; and 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on disposable absorbent article or may be one or more separate elements joined directly or indirectly with one or more elements of the disposable absorbent article. Further, the sublayer may include a structure that is separate from the absorbent core or may include or be part of at least a portion of the absorbent core.

Suitable exemplary materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Embodiments of the present invention may also include pockets for receiving and containing waste, spacers which provide voids for waste, barriers for limiting the movement of waste in the article, compartments or voids which accept and contain waste materials deposited in the pull-on disposable absorbent article, and the like, or any combinations thereof. Examples of pockets and spacers for use in absorbent products are described in U.S. Pat. Nos. 5,514,121; 5,171,236; 5,397,318; 5,540,671; 6,168,584; 5,306,266; and 5,997,520. Examples of compartments or voids in an absorbent article are disclosed in U.S. Pat. Nos. 4,968,312; 4,990,147; 5,062,840; and 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. Nos. 5,941,864; 5,977,430; and 6,013,063.

Embodiments of the present invention may include acquisition/distribution layers which can be configured to distribute moisture from a wetness event to moisture responsive members within the disposable absorbent article. Examples of suitable acquisition/distribution layers are described in U.S. Pat. No. 5,460,622, U.S. Patent Application Publication No. 2005/0027267, and U.S. Patent Application Publication No. 2005/009173.

Embodiments of the present invention may include a dusting layer which is well known in the art. Examples of suitable dusting layers are discussed in U.S. Pat. No. 4,888,231.

As shown in FIG. 9, a disposable absorbent article 600 may be separated from a siamese web 999 via a product separation boundary 645. As shown, in some embodiments the siamese web 999 can be used to construct a sanitary napkin 600. As shown, in some embodiments, the siamese web 999 can be cut along the product separation boundary 645 which resembles a sanitary napkin. In some embodiments, the product separation boundary 645 can extend through the fastening element 416A such that a first wing 920A comprises a portion of the fastening element 416A. Similarly, in some embodiments, the product separation boundary 645 can extend through the fastening element 416B such that a second wing 920B may comprise a portion of the fastening element 416B. As shown, in some embodiments, the product separation boundary 645 can generally follow an outer periphery of the sanitary napkin 600 such that after the separation process is completed, a sanitary napkin may be formed.

In some embodiments, the fastening elements 416A and 416B can be configured such that they engage one another and wrap around an undergarment, thereby securing the sanitary napkin 600 in place. In some embodiments, the fastening element 416A and 416B may comprise complimentary fastening elements.

As shown, in some embodiments, the first wing 920A may comprise a portion of the end region 420A. Similarly, in some embodiments, the second wing 920B may comprise a portion of the end region 420B. The body of the sanitary napkin 600 may comprise a portion of each panel region 410A and 410B.

An absorbent core 632 can be placed on the siamese web 999. Additionally, a topsheet, not shown, can subsequently be placed on the siamese web 999, thereby creating the sanitary napkin 600. Exemplary sanitary napkins and their materials are described in U.S. Patent Application Publication No. 2005/0004547.

As shown heretofore, the fastening elements have extended the full length of the portions of parent web, fastening member web, siamese webs and/or single repeating unit webs, shown. In some embodiments, the fastening elements of the fastening member of the present invention may extend the full length of the webs on which the fastening elements are disposed. Alternatively, in some embodiments, the fastening elements may comprise discrete fastening elements placed along the length of the web.

Any suitable fastening elements known in the art can be used in the present invention. Examples of suitable fastening elements include engaging components, receiving components, adhesive components, cohesive components, the like, or any suitable combination thereof.

An example of a suitable engaging component may comprise hook fastening material. The hook fastening material can mechanically engage fibrous elements of a receiving element so as to provide a secure closure. A hook fastening material according to the present invention may be manufactured from a wide range of materials. Examples of suitable materials include nylon, polyester, polypropylene, or any combination of these materials, or other materials as are known in the art.

A suitable hook fastening material comprises a number of shaped engaging elements projecting from a backing such as the commercially available material designated Scotchmate™ brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815. Another suitable hook fastening material comprises an array of prongs formed of thermoplastic material. Hot melt adhesive thermoplastics, in particular polyester and polyamide hot melt adhesives, are particularly well suited for forming the prongs of the hook fastening material. The prongs, in some embodiments, can be manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087. In some embodiments, the hooks can be thermoplastically printed. Examples of suitable hook printing processes are described in U.S. Pat. No. 5,540,673 and in WO 2004/082918.

An example of a suitable receiving component may comprise a plurality of loops. Loop fastening material and a method for making the same are described in U.S. Pat. Nos. 5,380,313; 5,569,233; 5,407,439; 5,542,942; 5,669,900; 5,318,555; U.S. Application Publication No. 2003/0077430; and WO 04/030763.

An example of a suitable adhesive component may comprise discrete tape tabs. An example of a suitable tape tab is available from the 3M Corporation of St. Paul, Minn., U.S.A. under the designation of XMF99121.

An example of a suitable cohesive component may comprise cohesive fastening patches. In some embodiments, the cohesive fastening patches may be formed of an inherently crystalline water-based synthetic elastomer to which a tackifying agent has been added to disrupt the polycrystalline structure and thereby render the elastomer cohesive. Exemplary synthetic cohesive products are available from Andover Coated Products, Incorporated, of Salisbury, Mass., U.S.A. and are described in U.S. Pat. No. 6,156,424.

Test Methods:

Extensibility

Force at elongation is measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with diamond faced grips, wider than the width of the test specimen.

Equilibrate samples in a conditioned room maintained at about 23±2° C. and about 50±2% relative humidity for at least two hours before testing. Herein width of the sample is defined as dimension 491 and length is defined as dimension 490 according to FIG. 1B.

Choose two matching fastening members 100 and label them Specimen A and Specimen B. On Specimen A, determine and mark the proximal edge of the stiffening element at 110B. Determine and mark the proximal edge of the stretch region 110C. For example, marks can be placed 1 mm apart along the width of the stretch region where the 110C boundary is suspected to be. By hand, gently (<20 gf) pull 1 cm segments along that edge to detect the boundary where the marks remain at 1 mm and where they spread apart. Measure the width of the stretch region 134 to the nearest 1 mm. Using a scalpel, cut a strip 2.54 mm long 490 from the center of specimen that extends its entire width 491. Trim the width 491 of the strip leaving at least 5 mm extending from both ends 110B and 110C to clamp in the grip faces. On the matching Specimen B, once again determine and mark the proximal edge of the stiffening element at 110B. Measure the distance 133 from 110B to the proximal edge of the fastening element 302 to the nearest 1 mm. Using a scalpel, cut a strip 2.54 mm long 490 from the center of specimen that extends its entire width 491. Trim the width 491 of the strip leaving at least 5 mm extending from both ends 302 and 110B to clamp in the grip faces.

Set the gauge length of the tensile tester to distance 134. Zero the crosshead and load the cell. Insert Specimen A into the upper grips aligning it along 110B and close the upper grips. Insert the specimen into the lower grips aligning it along 110C and close. The specimen should be aligned vertically without skew, and under enough tension to eliminate any slack, but less than 0.05N of force on the load cell. Start the tensile tester and data collection. The jaws are moved apart at a rate of 127 mm/min to the desired % elongation. Herein, % Elongation is defined as the extension divided by the gauge length, multiplied by 100. Reset the gauge length to distance 133 and run Specimen B in like fashion aligning the specimen at 302 and 110B in the grips.

The force at the desired % elongation is calculated by the software from the resulting force/elongation curves. Results are calculated as Force in Newtons at the target elongation divided by the length (direction 490) of the specimen in mm, and reported to the nearest 0.01 N/mm.

Stiffness

Figure 10:
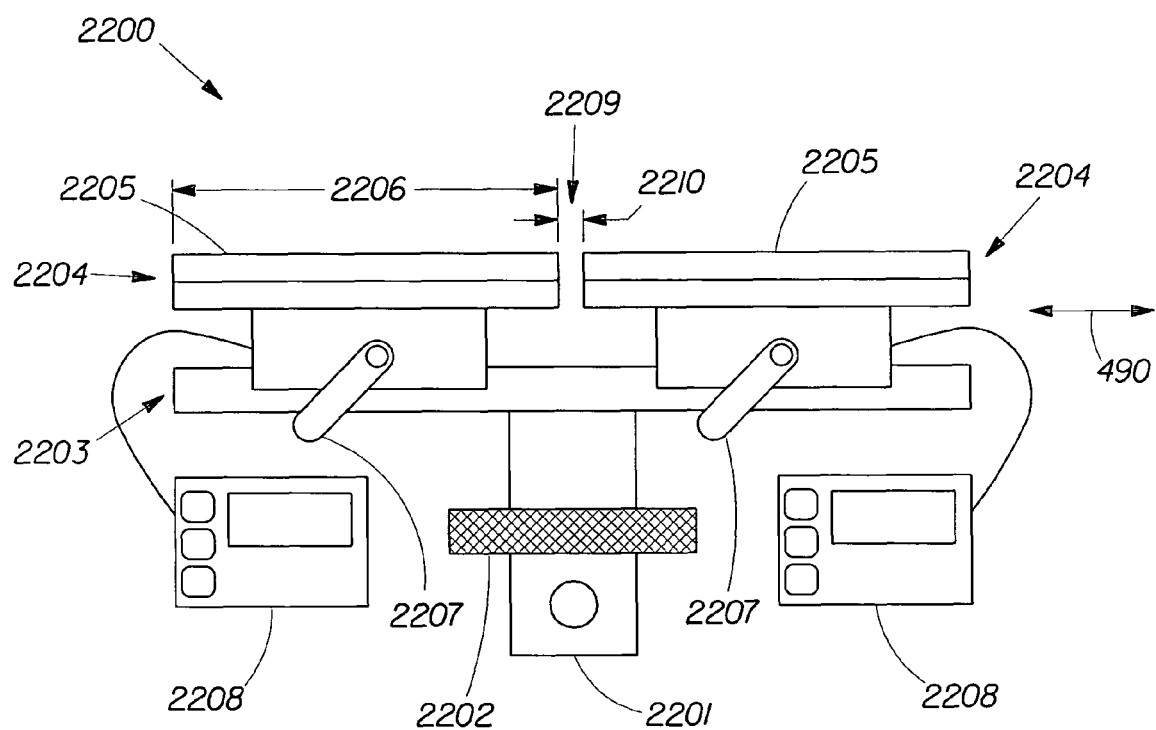
FIG. 10 is an elevation view showing an apparatus for testing the stiffness of materials.
Figure 11A:
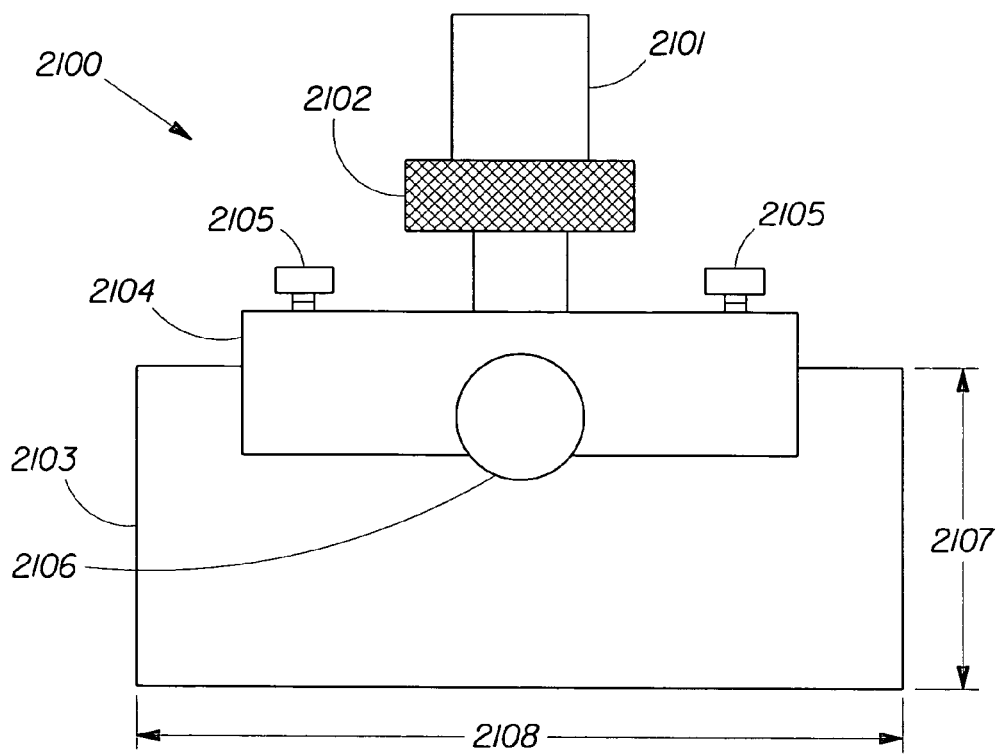
FIG. 11A is a front elevation view showing a plunger for use with the apparatus of FIG. 10.
Figure 11B:
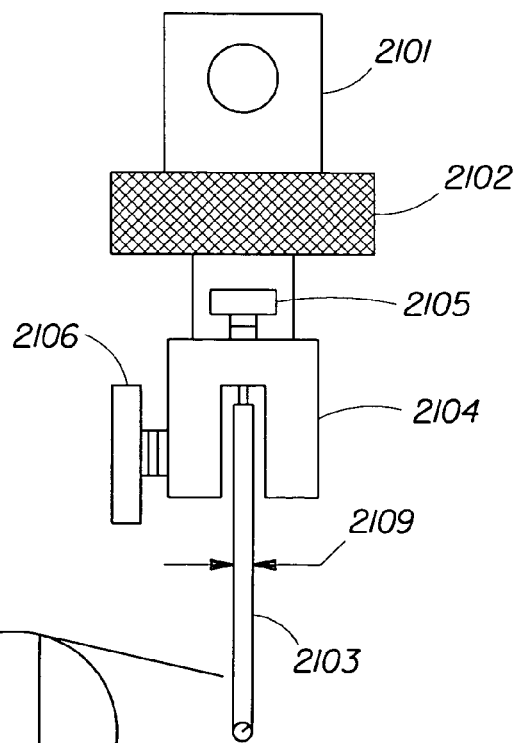
FIG. 11B is a side elevation view showing a plunger for use with the apparatus of FIG. 10.

Stiffness is measured using a constant rate of extension tensile tester with computer interface (a suitable instrument is a MTS Alliance under TestWorks 4 software, as available from MTS Systems Corp., Eden Prairie, Minn.) fitted with a 10 N load cell. A plunger blade 2100, shown in FIG. 11A (front view) and FIG. 11B (side view), is used for the upper movable test fixture. Base support platforms 2200, shown in FIG. 10, are used as the lower stationary test fixture. All testing is performed in a conditioned room maintained at about 23° C.±2° C. and about 50%±2% relative humidity. Herein, width of the sample is defined as dimension 491 and length is defined as dimension 490 according to FIG. 1B.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 3.25 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 8.00±0.02 mm between the two gap edges of the support platforms 2204, with the plunger blade 2103 accurately (±0.02 mm) centered in the gap. Program the tensile tester for a compression test. Set the gauge length from the bottom of the plunger blade 2103 to the top surface of the support platform 2204 to 15 mm. Set the crosshead to lower at 500 mm/min for a distance of 25 mm. Set the data acquisition rate to 200 Hz.

Precondition samples at about 23° C.±2° C. and about 50%±2% relative humidity for 2 hours prior to testing. Die cut a test specimen 13 mm in width (direction 491) by 25.4 mm in length (direction 490). If the element is not 13 mm in width, use the full width of the element. Examine the specimen for any exposed adhesive and deactivate by applying baby powder where necessary. Place the specimen flat onto the surface of the support platform 2204 over the gap 2209 with the fastening element facing upward. If the particular specimen does not contain a fastening element, orient the specimen such that the fastening element side is facing up. Center the specimen across the gap, its length (direction 490, indicated on FIG. 10) should be parallel to the gap and its width (direction 491) should be perpendicular to the gap. Zero the load cell; start the tensile tester and the data acquisition.

Figure 12:
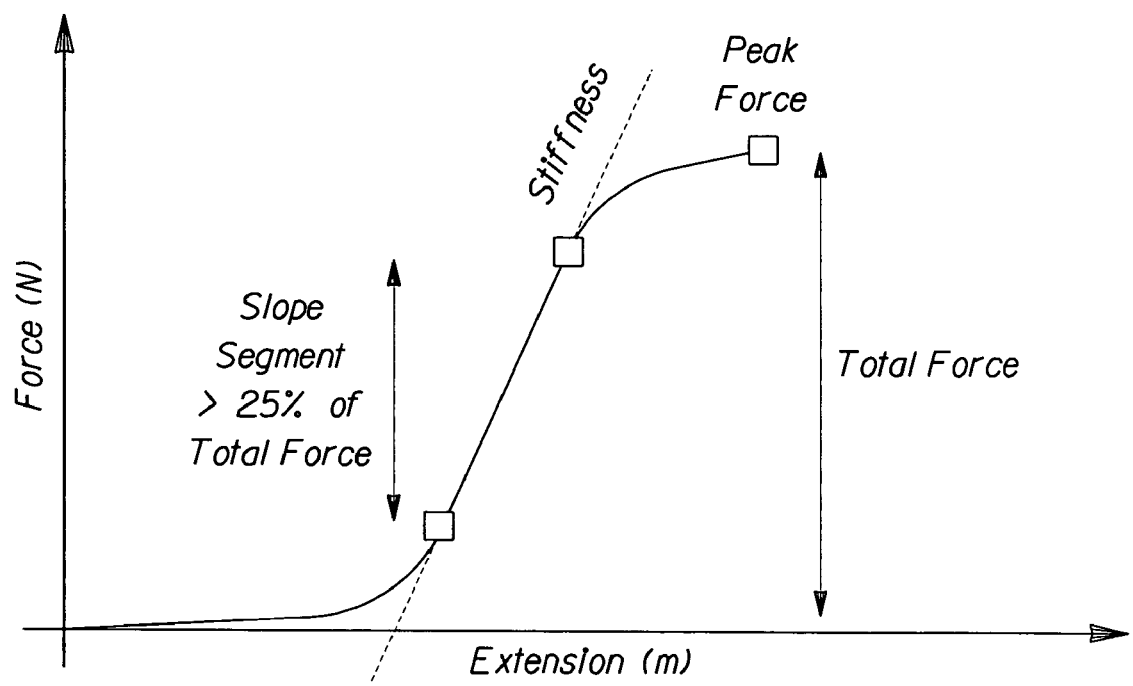
FIG. 12 is a graph showing Peak load and slope calculation areas on bending curve.

Program the software to calculate the maximum peak force (N) and stiffness (N/m) from the constructed force (N) verses extension (m) curve. Stiffness is calculated as the slope of the force/extension curve for the linear region of the curve (see FIG. 12), using a minimum line segment of at least 25% of the total peak force to calculate the slope. If the width of the element is not 13 mm, normalize the actual width to 13 mm as follows:

$$\text{Stiffness}_{(actual\ length)} = [\text{Stiffness}_{(13\ mm)}/13\ \text{mm}] \times \text{actual width (mm)}$$

$$\text{Peak Force}_{(actual\ length)} = [\text{Peak Force}_{(13\ mm)}/13\ \text{mm}] \times \text{actual width (mm)}$$

Report peak force to the nearest 0.1 N and the stiffness to the nearest 0.1 N/m.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fastening member having an inboard end and an outboard end, the fastening member comprising:
    at least one substrate layer;
    a panel region disposed adjacent to the inboard end;
    an end region disposed adjacent to the outboard end, wherein the end region comprises a fastening element zone having a first stiffness and an intermediate zone having a second stiffness, wherein the intermediate zone is disposed between the fastening element zone and the panel region adjacent to an interface between the panel region and the end region; and
    a fastening element disposed in the end region and defining the fastening element zone,
    wherein the panel region extends to greater than about 100% under an applied load of about 0.5 N/cm and the end region extends to less than about 100% at an applied load of about 4.0 N/cm, and wherein the first stiffness is greater than the second stiffness;
    wherein the substrate layer is folded such that a folded portion of the substrate layer is disposed underneath the fastening element zone.

2. The fastening member of claim 1, wherein the first stiffness is greater than about 1000 N/m and the second stiffness is less than about 1000 N/m.

3. The fastening member of claim 1, wherein the first stiffness is greater than about 1000 N/m and less than about 7000 N/m.

4. The fastening member of claim 1, wherein the first stiffness is greater than about 1500 N/m and less than about 6000 N/m.

5. The fastening member of claim 1, wherein the first stiffness is greater than about 2500 N/m and less than about 5000 N/m.

6. The fastening member of claim 1, wherein the fastening element comprises a plurality of hooks.

7. The fastening member of claim 1 further comprising a grip zone disposed adjacent the outboard end of the fastening member such that the fastening element zone is disposed between the intermediate zone and the grip zone.

8. The fastening member of claim 1 wherein the panel region has a third stiffness and wherein the second stiffness is greater than the third stiffness.

9. A web of fastening members, the web having a first longitudinal edge and a second longitudinal edge, the web of fastening members further comprising:
    at least one substrate layer;
    a first panel region disposed adjacent to the first longitudinal edge;
    a second panel region disposed adjacent to the second longitudinal edge; and
    an end area disposed between the first panel region and the second panel region the end area comprising:
        a fastening element defining a fastening element zone having a first stiffness;
        a first intermediate zone disposed between the fastening element zone and the first panel region, the first intermediate zone having a second stiffness; and
        a second intermediate zone disposed between the fastening element zone and the second panel region, the second intermediate zone having a third stiffness;
    wherein the first panel region and the second panel region each extends to greater than about 100% under an applied load of about 0.5 N/cm and the end area, extends to less than about 100% at an applied load of about 4 N/cm, and wherein the first stiffness is greater than the second stiffness and greater than the third stiffness;
    wherein the substrate layer is folded such that a folded portion of the substrate layer is disposed underneath the fastening element zone.

10. The web of fastening members of claim 9, wherein the first stiffness is greater than about 1000 N/m and the second stiffness is less than about 1000 N/m.

11. The web of fastening members of claim 9, wherein the first stiffness is greater than about 1000 N/m and less than about 7000 N/m.

12. The web of fastening members of claim 9, wherein the first stiffness is greater than about 1500 N/m and less than about 6000 N/m.

13. The web of fastening members of claim 9, wherein the first stiffness is greater than about 2500 N/m and less than about 5000 N/m.

14. The web of fastening members of claim 9 wherein the fastening element comprises a plurality of hooks.

15. The fastening member of claim 1 wherein the end region, including said fastening element zone and said intermediate zone, extends to less than about 50% at an applied load of about 4.0 N/cm.

16. The web of fastening members of claim 9 wherein the end region, including said fastening element zone and said intermediate zones, extends to less than about 50% at an applied load of about 4 N/cm.

* * * * *